United States Patent
Tang et al.

(10) Patent No.: US 8,614,067 B2
(45) Date of Patent: *Dec. 24, 2013

(54) POLYPEPTIDES HAVING CELLULOLYTIC ENHANCING ACTIVITY AND POLYNUCLEOTIDES ENCODING SAME

(71) Applicants: Novozymes A/S, Bagsvaerd (DK); Novozymes, Inc., Davis, CA (US)

(72) Inventors: Lan Tang, Beijing (CN); Ye Liu, Beijing (CN); Junxin Duan, Beijing (CN); Yu Zhang, Beijing (CN); Christian Isak Jorgensen, Bagsvaerd (DK); Randall Kramer, Lincoln, CA (US)

(73) Assignees: Novozymes A/S, Bagsvaerd (DK); Novozymes, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/857,014

(22) Filed: Apr. 4, 2013

(65) Prior Publication Data

US 2013/0217078 A1    Aug. 22, 2013

Related U.S. Application Data

(60) Continuation of application No. 13/548,726, filed on Jul. 13, 2012, now Pat. No. 8,420,351, which is a division of application No. 13/434,108, filed on Mar. 29, 2012, now Pat. No. 8,242,329, which is a division of application No. 12/893,536, filed on Sep. 29, 2010, now Pat. No. 8,148,103.

(60) Provisional application No. 61/246,893, filed on Sep. 29, 2009.

(51) Int. Cl.
*C12P 1/00* (2006.01)
*C07K 14/00* (2006.01)
*C11D 3/02* (2006.01)

(52) U.S. Cl.
USPC ............. 435/41; 530/350; 435/267; 510/108

(58) Field of Classification Search
None
See application file for complete search history.

(56) References Cited

U.S. PATENT DOCUMENTS

2008/0299613 A1    12/2008    Merino et al.

FOREIGN PATENT DOCUMENTS

| WO | 2005074647 A2 | 8/2005 |
| WO | 2005074656 A2 | 8/2005 |
| WO | 2007089290 A2 | 8/2007 |
| WO | 2008148131 A1 | 12/2008 |

OTHER PUBLICATIONS

Dotson et al., 2005, Epofetch, Access No. AEC05921.
Dotson et al., 2005, Epofetch, Access No. AEC05922.
Merino et al., 2009, Epofetch, Access No. AUL87130.
Merino et al., 2009, Epofetch, Access No. AUL87131.

*Primary Examiner* — Nashaat T. Nashed
(74) *Attorney, Agent, or Firm* — Robert L. Starnes

(57) ABSTRACT

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

14 Claims, 3 Drawing Sheets

```
      M   L   S   S       T   T   R       T   L   A       F   T   G   L       A   G   L       L   S   A
  1 ATGCTGTCTT CGACGACTCG CACCCTCGCC TTTACAGGCC TTGCGGGCCT TCTGTCCGCT
      P   L   V   K       A   H   G       F   V   Q       G   I   V   I       G   D   Q       F
 61 CCCCTGGTCA AGGCCCATGG CTTTGTCCAG GGCATTGTCA TCGGTGACCA ATTGTAAGTC

121 CCTCTCTTGC AGTTCTGTCG ATTAACTGCT GGACTGCTTG CTTGACTCCC TGCTGACTCC
              Y   S   G   Y   I   V   N   S       F   P   Y       E   S   N       P   P   V  ·
181 CAACAGCTAC AGCGGGTACA TCGTCAACTC GTTCCCCTAC GAATCCAACC CACCCCCCGT
    ·  I   G   W       A   T   T       A   D   L       G   F   V       D   G   T       Y   Q   G  ·
241 CATCGGCTGG GCCACGACCG CCACCGACCT GGGCTTCGTC GACGGCACAG GATACCAAGG
    ·  P   D   I       I   C   H   R       N   A   T       P   A   P       L   T   A       V   A   A  ·
301 CCCGGACATC ATCTGCCACC GGAATGCGAC GCCCGCGCCG CTGACAGCCC CCGTGGCCGC
    ·  G   G   T       V   E   L   Q       W   T   P       W   P   D       S   H   H   G       P   V   I  ·
361 CGGCGGCACC GTCGAGCTGC AGTGGACGCC GTGGCCGGAC AGCCACCACG GACCCGTCAT
    ·  T   Y   L       A   P   C   N       G   N   C       S   T   V       D   K   T   T       L   E   F  ·
421 CACCTACCTG GCGCCGTGCA ACGGCAACTG CTCGACCGTC GACAAGACGA CGCTGGAGTT
    ·  F   K   I       D   Q   Q   G       L   I   D       D   T   S       P   P   G   T       W   A   S  ·
481 CTTCAAGATC GACCAGCAGG GCCTGATCGA CGACACGAGC CCGCCGGGCA CCTGGGCGTC
    ·  D   N   L       I   A   N   N       S   W       T   V   T       I   P   N   S       V   A   P  ·
541 GGACAACCTC ATCGCCAACA ACAATAGCTG GACCGTCACC ATTCCCAACA GCGTCGCCCC
    ·  G   N   Y       V   L   R   H       E   I   I       A   L   H       S   A   N   N       K   D   G  ·
601 CGGCAACTAC GTCCTGCGCC ACGAGATCAT CGCCCTGCAC TCGGCCAACA ACAAGGACGG
    ·  A   Q   N       Y   P   Q   C       I   N   I       E   V   T       G   G   G   S       D   A   P  ·
661 CGCCCAGAAC TACCCCCAGT GCATCAACAT CGAGGTCACG GGCGGCGGCT CCGACGCGCC
    ·  E   G   T       L   G   E   D       L   Y   H       D   T   D       P   G   I   L       V   D   I  ·
721 TGAGGGTACT CTGGGCGAGG ATCTCTACCA TGACACCGAC CCGGGCATTC TGGTCGACAT
    ·  Y   E   P       I   A   T   Y       T   I   P       G   P   P       E   P   T       F   *
781 TTACGAGCCC ATTGCGACGT ATACCATTCC GGGGCCGCCT GAGCCGACGT TCTAG
```

FIG. 2

POLYPEPTIDES HAVING CELLULOLYTIC ENHANCING ACTIVITY AND POLYNUCLEOTIDES ENCODING SAME

CROSS-REFERENCE TO RELATED APPLICATIONS

This application is a continuation of U.S. application Ser. No. 13/548,726 filed Jul. 13, 2012, which is a divisional of U.S. application Ser. No. 13/434,108 filed on Mar. 29, 2012, which is a divisional of U.S. application Ser. No. 12/893,536 filed on Sep. 29, 2010, now U.S. Pat. No. 8,148,103, which claims the benefit of U.S. Provisional Application 61/246,893 filed on Sep. 29, 2009, which applications are incorporated herein by reference.

STATEMENT AS TO RIGHTS TO INVENTIONS MADE UNDER FEDERALLY SPONSORED RESEARCH AND DEVELOPMENT

This invention was made in part with Government support under Cooperative Agreement DE-FC36-08GO18080 awarded by the Department of Energy. The government has certain rights in this invention.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference.

BACKGROUND OF THE INVENTION

1. Field of the Invention

The present invention relates to isolated polypeptides having cellulolytic enhancing activity and isolated polynucleotides encoding the polypeptides. The invention also relates to nucleic acid constructs, vectors, and host cells comprising the polynucleotides as well as methods of producing and using the polypeptides.

2. Description of the Related Art

Cellulose is a polymer of the simple sugar glucose linked by beta-1,4 bonds. Many microorganisms produce enzymes that hydrolyze beta-linked glucans. These enzymes include endoglucanases, cellobiohydrolases, and beta-glucosidases. Endoglucanases digest the cellulose polymer at random locations, opening it to attack by cellobiohydrolases. Cellobiohydrolases sequentially release molecules of cellobiose from the ends of the cellulose polymer. Cellobiose is a water-soluble beta-1,4-linked dimer of glucose. Beta-glucosidases hydrolyze cellobiose to glucose.

The conversion of lignocellulosic feedstocks into ethanol has the advantages of the ready availability of large amounts of feedstock, the desirability of avoiding burning or land filling the materials, and the cleanliness of the ethanol fuel. Wood, agricultural residues, herbaceous crops, and municipal solid wastes have been considered as feedstocks for ethanol production. These materials primarily consist of cellulose, hemicellulose, and lignin. Once the cellulose is converted to glucose, the glucose is easily fermented by yeast into ethanol.

It would be advantageous in the art to improve the ability to enzymatically degrade lignocellulosic feedstocks.

WO 2005/074647 discloses isolated polypeptides having cellulolytic enhancing activity and polynucleotides thereof from *Thielavia terrestris*. WO 2005/074656 discloses an isolated polypeptide having cellulolytic enhancing activity and the polynucleotide thereof from *Thermoascus aurantiacus*. WO 2007/089290 discloses an isolated polypeptide having cellulolytic enhancing activity and the polynucleotide thereof from *Trichoderma reesei*.

The present invention provides polypeptides having cellulolytic enhancing activity and polynucleotides encoding the polypeptides.

SUMMARY OF THE INVENTION

The present invention relates to isolated polypeptides having cellulolytic enhancing activity selected from the group consisting of:

(a) a polypeptide comprising an amino acid sequence having at least 80% identity to the mature polypeptide of SEQ ID NO: 2;

(b) a polypeptide encoded by a polynucleotide that hybridizes under high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polypeptide encoded by a polynucleotide comprising a nucleotide sequence having at least 80% identity to the mature polypeptide coding sequence of SEQ ID NO: 1; and (d) a variant comprising a substitution, deletion, and/or insertion of one or more (several) amino acids of the mature polypeptide of SEQ ID NO: 2.

The present invention also relates to isolated polynucleotides encoding polypeptides having cellulolytic enhancing activity, selected from the group consisting of:

(a) a polynucleotide encoding a polypeptide comprising an amino acid sequence having at least 80% identity to the mature polypeptide of SEQ ID NO: 2;

(b) a polynucleotide that hybridizes under at least high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii);

(c) a polynucleotide comprising a nucleotide sequence having at least 80% identity to the mature polypeptide coding sequence of SEQ ID NO: 1; and (d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing the polypeptides having cellulolytic enhancing activity.

The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. The present also relates to such a double-stranded inhibitory RNA (dsRNA) molecule, wherein optionally the dsRNA is a siRNA or a miRNA molecule.

The present invention also relates to methods for degrading or converting a cellulosic material, comprising: treating the cellulosic material with an enzyme composition in the presence of a polypeptide having cellulolytic enhancing activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more fermenting microorganisms to produce the fermentation product; and (c) recovering the fermentation product from the fermentation.

The present invention also relates to methods of fermenting a cellulosic material, comprising: fermenting the cellulosic material with one or more fermenting microorganisms, wherein the cellulosic material is saccharified with an enzyme composition in the presence of a polypeptide having cellulolytic enhancing activity of the present invention. In a preferred aspect, the fermenting of the cellulosic material produces a fermentation product. In one aspect, the method further comprises recovering the fermentation product from the fermentation.

The present invention also relates to plants comprising an isolated polynucleotide encoding a polypeptide having cellulolytic enhancing activity.

The present invention also relates to methods of producing a polypeptide having cellulolytic enhancing activity, comprising: (a) cultivating a transgenic plant or a plant cell comprising a polynucleotide encoding the polypeptide having cellulolytic enhancing activity under conditions conducive for production of the polypeptide; and (b) recovering the polypeptide.

The present invention further relates to an isolated polynucleotide encoding a signal peptide comprising or consisting of amino acids 1 to 25 of SEQ ID NO: 2; to nucleic acid constructs, expression vectors, and recombinant host cells comprising the polynucleotides; and to methods of producing a protein.

BRIEF DESCRIPTION OF THE FIGURES

FIG. 2 shows the genomic DNA sequence and the deduced amino acid sequence of a gene encoding a *Penicillium* sp. GH61A polypeptide having cellulolytic enhancing activity (SEQ ID NOs: 1 and 2, respectively).

DEFINITIONS

Figure 1:
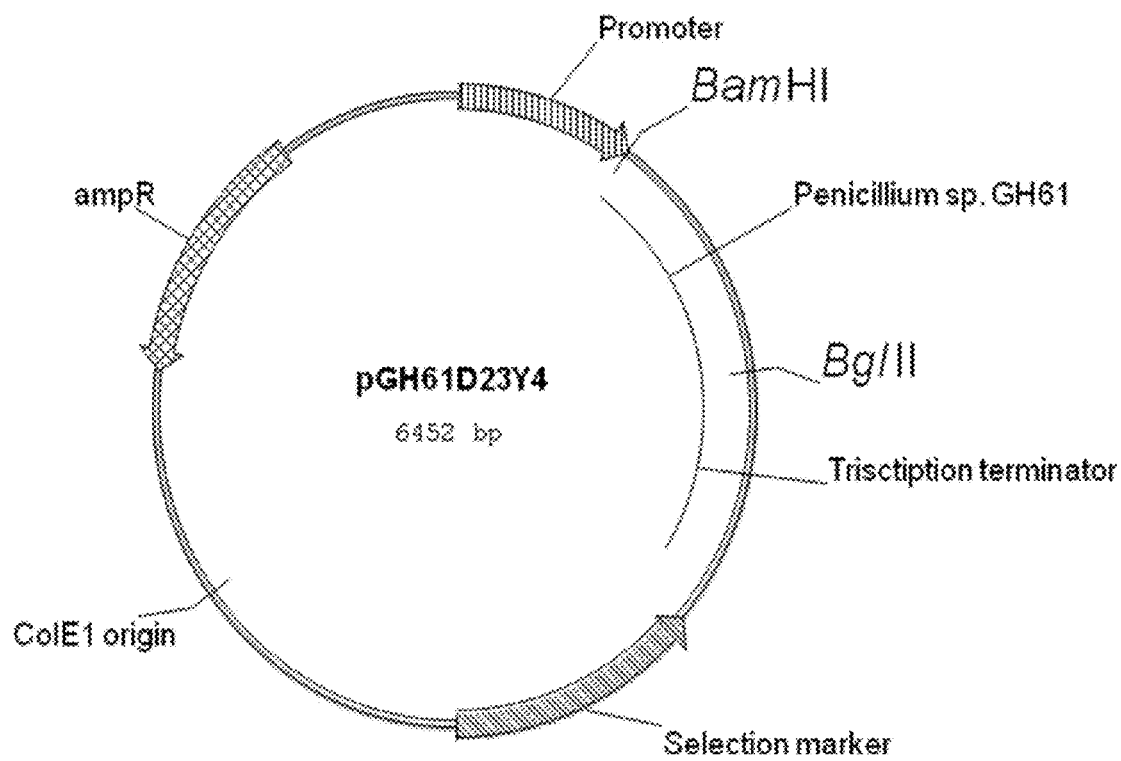
FIG. 1 shows a map of pGH61 D23Y4.

Polypeptide Having Cellulolytic Enhancing Activity: The term "polypeptide having cellulolytic enhancing activity" means a GH61 polypeptide that enhances the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at 50° C. compared to a control hydrolysis with equal total protein loading without cellulolytic enhancing activity (1-50 mg of cellulolytic protein/g of cellulose in PCS). In a preferred aspect, a mixture of CELLUCLAST® 1.5 L (Novozymes NS, Bagsvrd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The polypeptides having cellulolytic enhancing activity have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the cellulolytic enhancing activity of the mature polypeptide of SEQ ID NO: 2.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, more preferably at least 1.05-fold, more preferably at least 1.10-fold, more preferably at least 1.25-fold, more preferably at least 1.5-fold, more preferably at least 2-fold, more preferably at least 3-fold, more preferably at least 4-fold, more preferably at least 5-fold, even more preferably at least 10-fold, and most preferably at least 20-fold.

Family 61 Glycoside Hydrolase: The term "Family 61 glycoside hydrolase" or "Family GH61" is defined herein as a polypeptide falling into the glycoside hydrolase Family 61 according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Cellulolytic Enzyme or Cellulase: The term "cellulolytic enzyme" or "cellulase" means one or more (several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-20 mg of cellulolytic enzyme protein/g of cellulose in PCS for 3-7 days at 50° C. compared to a control hydrolysis without addition of cellulolytic enzyme protein. Typical conditions are 1 ml reactions, washed or unwashed PCS, 5% insoluble solids, 50 mM sodium acetate pH 5, 1 mM MnSO$_4$, 50° C., 72 hours, sugar analysis by AMINEX® HPX-87H column (Bio-Rad Laboratories, Inc., Hercules, Calif., USA).

Endoglucanase: The term "endoglucanase" is defined herein as an endo-1,4-(1,3;1,4)-beta-D-glucan 4-glucanohydrolase (E.C. 3.2.1.4), which catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined based on reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) hydrolysis according to the procedure of Ghose, 1987, *Pure and Appl. Chem.* 59: 257-268.

Cellobiohydrolase: The term "cellobiohydrolase" is defined herein as a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). For purposes of the present invention, cellobiohydrolase activity is determined on a fluorescent disaccharide derivative 4-methylumbelliferyl-β-D-lactoside according to the procedures described by van Tilbeurgh et al., 1982, *FEBS Letters* 149: 152-156 and van Tilbeurgh and Claeyssens, 1985, *FEBS Letters* 187: 283-288.

Beta-Glucosidase: The term "beta-glucosidase" is defined herein as a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, Extracellular beta-D-glucosidase from *Chaetomium thermophilum* var. *coprophilum*: production, purification and some biochemical properties, *J. Basic Microbiol.* 42: 55-66, except different conditions were employed as described herein. One unit of beta-glucosidase activity is defined as 1.0 μmole of p-nitrophenol produced per minute at 40° C., pH 5 from 1 mM p-nitrophenyl-beta-D-glucopyranoside as substrate in 100 mM sodium citrate pH 5 containing 0.01% TWEEN® 20.

Xylan Degrading Activity: The terms "xylan degrading activity" or "xylanolytic activity" are defined herein as a biological activity that hydrolyzes xylan-containing material. The two basic approaches for measuring xylanolytic activity include: (1) measuring the total xylanolytic activity, and (2) measuring the individual xylanolytic activities (endoxylanases, beta-xylosidases, arabinofuranosidases, alpha-glucuronidases, acetyl xylan esterases, ferulic acid esterases, and alpha-glucuronyl esterases). Recent progress in assays of xylanolytic enzymes is summarized in several publications including Biely and Puchard, Recent progress in the assays of xylanolytic enzymes, 2006, *Journal of the Science of Food and Agriculture* 86(11): 1636-1647; Spanikova and Biely, 2006, Glucuronoyl esterase—Novel carbohydrate esterase produced by *Schizophyllum commune*, *FEBS Letters* 580 (19): 4597-4601; and Herrmann, Vrsanska, Jurickova, Hirsch, Biely, and Kubicek, 1997, The beta-D-xylosidase of *Trichoderma reesei* is a multifunctional beta-D-xylan xylohydrolase, *Biochemical Journal* 321: 375-381.

Total xylan degrading activity can be measured by determining the reducing sugars formed from various types of xylan, including oat spelt, beechwood, and larchwood xylans, or by photometric determination of dyed xylan fragments released from various covalently dyed xylans. The most common total xylanolytic activity assay is based on production of reducing sugars from polymeric 4-O-methyl glucuronoxylan as described in Bailey, Biely, Poutanen, 1992, Interlaboratory testing of methods for assay of xylanase activity, *Journal of Biotechnology* 23(3): 257-270.

For purposes of the present invention, xylan degrading activity is determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using a p-hydroxybenzoic acid hydrazide (PHBAH) assay as described by Lever, 1972, A new reaction for colorimetric determination of carbohydrates, *Anal. Biochem* 47: 273-279.

Xylanase: The term "xylanase" is defined herein as a 1,4-beta-D-xylan-xylohydrolase (E.C. 3.2.1.8) that catalyzes the endo-hydrolysis of 1,4-beta-D-xylosidic linkages in xylans. For purposes of the present invention, xylanase activity is determined using birchwood xylan as substrate. One unit of xylanase activity is defined as 1.0 μmole of reducing sugar (measured in glucose equivalents as described by Lever, 1972, A new reaction for colorimetric determination of carbohydrates, *Anal. Biochem* 47: 273-279) produced per minute during the initial period of hydrolysis at 50° C., pH 5 from 2 g of birchwood xylan per liter as substrate in 50 mM sodium acetate pH 5 containing 0.01% TWEEN® 20.

Beta-Xylosidase: The term "beta-xylosidase" is defined herein as a beta-D-xyloside xylohydrolase (E.C. 3.2.1.37) that catalyzes the exo-hydrolysis of short beta (1→4)-xylooligosaccharides, to remove successive D-xylose residues from the non-reducing termini. For purposes of the present invention, one unit of beta-xylosidase activity is defined as 1.0 μmole of p-nitrophenol produced per minute at 40° C., pH 5 from 1 mM p-nitrophenyl-beta-D-xyloside as substrate in 100 mM sodium citrate pH 5 containing 0.01% TWEEN® 20.

Acetylxylan Esterase: The term "acetylxylan esterase" is defined herein as a carboxylesterase (EC 3.1.1.72) that catalyses the hydrolysis of acetyl groups from polymeric xylan, acetylated xylose, acetylated glucose, alpha-napthyl acetate, and p-nitrophenyl acetate. For purposes of the present invention, acetylxylan esterase activity is determined using 0.5 mM p-nitrophenylacetate as substrate in 50 mM sodium acetate pH 5.0 containing 0.01% TWEEN™ 20. One unit of acetylxylan esterase activity was defined as the amount of enzyme capable of releasing 1 μmole of p-nitrophenolate anion per minute at pH 5, 25° C.

Feruloyl Esterase: The term "feruloyl esterase" is defined herein as a 4-hydroxy-3-methoxycinnamoyl-sugar hydrolase (EC 3.1.1.73) that catalyzes the hydrolysis of the 4-hydroxy-3-methoxycinnamoyl (feruloyl) group from an esterified sugar, which is usually arabinose in "natural" substrates, to produce ferulate (4-hydroxy-3-methoxycinnamate). Feruloyl esterase is also known as ferulic acid esterase, hydroxycinnamoyl esterase, FAE-III, cinnamoyl ester hydrolase, FAEA, cinnAE, FAE-I, or FAE-II. For purposes of the present invention, feruloyl esterase activity is determined using 0.5 mM p-nitrophenylferulate in 50 mM sodium acetate pH 5.0. One unit of feruloyl esterase activity equals the amount of enzyme capable of releasing 1 µmole of p-nitrophenolate anion per minute at pH 5, 25° C.

Alpha-Glucuronidase: The term "alpha-glucuronidase" is defined herein as an alpha-D-glucosiduronate glucuronohydrolase (EC 3.2.1.139) that catalyzes the hydrolysis of an alpha-D-glucuronoside to D-glucuronate and an alcohol. For purposes of the present invention, alpha-glucuronidase activity is determined according to de Vries, 1998, *J. Bacteriol.* 180: 243-249. One unit of alpha-glucuronidase activity equals the amount of enzyme capable of releasing 1 µmole of glucuronic acid or 4-O-methylglucuronic acid per minute at pH 5, 40° C.

Alpha-L-Arabinofuranosidase: The term "alpha-L-arabinofuranosidase" is defined herein as an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme activity acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. For purposes of the present invention, alpha-L-arabinofuranosidase activity is determined using 5 mg of medium viscosity wheat arabinoxylan (Megazyme International Ireland, Ltd., Bray, Co. Wicklow, Ireland) per ml of 100 mM sodium acetate pH 5 in a total volume of 200 µl for 30 minutes at 40° C. followed by arabinose analysis by AMINEX® HPX-87H column chromatography.

Cellulosic Material: The cellulosic material can be any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material can be, but is not limited to, herbaceous material, agricultural residue, forestry residue, municipal solid waste, waste paper, and pulp and paper mill residue (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is lignocellulose.

In one aspect, the cellulosic material is herbaceous material. In another aspect, the cellulosic material is agricultural residue. In another aspect, the cellulosic material is forestry residue. In another aspect, the cellulosic material is municipal solid waste. In another aspect, the cellulosic material is waste paper. In another aspect, the cellulosic material is pulp and paper mill residue.

In another aspect, the cellulosic material is corn stover. In another aspect, the cellulosic material is corn fiber. In another aspect, the cellulosic material is corn cob. In another aspect, the cellulosic material is orange peel. In another aspect, the cellulosic material is rice straw. In another aspect, the cellulosic material is wheat straw. In another aspect, the cellulosic material is switch grass. In another aspect, the cellulosic material is miscanthus. In another aspect, the cellulosic material is bagasse.

In another aspect, the cellulosic material is microcrystalline cellulose. In another aspect, the cellulosic material is bacterial cellulose. In another aspect, the cellulosic material is algal cellulose. In another aspect, the cellulosic material is cotton linter. In another aspect, the cellulosic material is amorphous phosphoric-acid treated cellulose. In another aspect, the cellulosic material is filter paper.

The cellulosic material may be used as is or may be subjected to pretreatment, using conventional methods known in the art, as described herein. In a preferred aspect, the cellulosic material is pretreated.

Pretreated Corn Stover: The term "PCS" or "Pretreated Corn Stover" is defined herein as a cellulosic material derived from corn stover by treatment with heat and dilute sulfuric acid.

Isolated Polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially Pure Polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature Polypeptide: The term "mature polypeptide" is defined herein as a polypeptide in its final form following translation and any post-translational modifications, such as N-terminal processing, C-terminal truncation, glycosylation, phosphorylation, etc. In one aspect, the mature polypeptide is amino acids 26 to 253 of SEQ ID NO: 2 based on the SignalP program (Nielsen et al., 1997, *Protein Engineering* 10:1-6) that predicts amino acids 1 to 25 of SEQ ID NO: 2 are a signal peptide.

Mature Polypeptide Coding Sequence: The term "mature polypeptide coding sequence" is defined herein as a nucleotide sequence that encodes a mature polypeptide having cellulolytic enhancing activity. In one aspect, the mature polypeptide coding sequence is nucleotides 76 to 832 of SEQ ID NO: 1 based on the SignalP program (Nielsen et al., 1997, supra) that predicts nucleotides 1 to 75 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment)

Homologous Sequence: The term "homologous sequence" is defined herein as a predicted protein having an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Penicillium* sp. polypeptide having cellulolytic enhancing activity of SEQ ID NO: 2 or the mature polypeptide thereof.

Polypeptide Fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has cellulolytic enhancing activity. In a preferred aspect, a fragment contains at least 200 amino acid residues, more preferably at least 210 amino acid residues, and most preferably at least 220 amino acid residues, of the mature polypeptide of SEQ ID NO: 2 or a homologous sequence thereof.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having cellulolytic enhancing activity. In a preferred aspect, a subsequence contains at least 600 nucleotides, more preferably at least 630 nucleotides, and most preferably at least 660 nucleotides of the mature polypeptide coding sequence of SEQ ID NO: 1 or a homologous sequence thereof.

Allelic Variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially Pure Polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99% pure, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding Sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that may be present in the corresponding genomic DNA. The initial, primary RNA transcript is a precursor to mRNA that is processed through a series of steps before appearing as mature spliced mRNA.

These steps include the removal of intron sequences by a process called splicing. cDNA derived from mRNA lacks, therefore, any intron sequences.

Nucleic Acid Construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control Sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably Linked: The term "operably linked" denotes herein a configuration in which a control sequence is placed at an appropriate position relative to the coding sequence of a polynucleotide sequence such that the control sequence directs the expression of the coding sequence of a polypeptide.

Expression: The term "expression" includes any step involved in the production of a polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide comprising or consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having cellulolytic enhancing activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Cellulolytic Enhancing Activity

In a first aspect, the present invention relates to isolated polypeptides comprising amino acid sequences having a degree of identity to the mature polypeptide of SEQ ID NO: 2 of preferably at least 80%, more preferably at least 85%, even more preferably at least 90%, most preferably at least 95%, and even most preferably at least 96%, at least 97%, at least 98%, or at least 99%, which have cellulolytic enhancing activity (hereinafter "homologous polypeptides"). In a preferred aspect, the homologous polypeptides comprise amino acid sequences that differ by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having cellulolytic enhancing activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 26 to 253 of SEQ ID NO: 2, or an allelic variant thereof; or a fragment thereof having cellulolytic enhancing activity. In another preferred aspect, the polypeptide comprises amino acids 26 to 253 of SEQ ID NO: 2. In another preferred aspect, the polypeptide consists of the amino acid sequence of SEQ ID NO: 2 or an allelic variant thereof; or a fragment thereof having cellulolytic enhancing activity. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 26 to 253 of SEQ ID NO: 2 or an allelic variant thereof; or a fragment thereof having cellulolytic enhancing activity. In another preferred aspect, the polypeptide consists of amino acids 26 to 253 of SEQ ID NO: 2.

In a second aspect, the present invention relates to isolated polypeptides having cellulolytic enhancing activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii) (J. Sambrook, E. F. Fritsch, and T. Maniatis, 1989, *Molecular Cloning, A Laboratory Manual*, 2d edition, Cold Spring Harbor, N.Y.). In a preferred aspect, the stringency conditions are high stringency conditions. In another preferred aspect, the stringency conditions are very high stringency conditions.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having cellulolytic enhancing activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may, therefore, be screened for DNA that hybridizes with the probes described above and encodes a polypeptide having cellulolytic enhancing activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1, or a subsequence thereof, the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the cDNA sequence contained in the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 76 to 832 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pGEM-T-GH61D23Y4 which is contained in *E. coli* DSM 22882, wherein the polynucleotide sequence thereof encodes a polypeptide having cellulolytic enhancing activity. In another preferred aspect, the nucleic acid probe is the mature polypeptide coding region contained in plasmid pGEM-T-GH61 D23Y4 which is contained in *E. coli* DSM 22882.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes of about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes of about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having cellulolytic enhancing activity encoded by polynucleotides comprising or consisting of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity. See polynucleotide section herein.

In a fourth aspect, the present invention relates to artificial variants comprising a substitution, deletion, and/or insertion of one or more (or several) amino acids of the mature polypeptide of SEQ ID NO: 2, or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., cellulolytic enhancing activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223, 409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2 is 10, preferably 9, more preferably 8, more preferably 7, more preferably at most 6, more preferably 5, more preferably 4, even more preferably 3, most preferably 2, and even most preferably 1.

Sources of Polypeptides Having Cellulolytic Enhancing Activity

A polypeptide having cellulolytic enhancing activity of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having cellulolytic enhancing activity of the present invention may be a bacterial polypeptide. For example, the polypeptide may be a gram positive bacterial polypeptide such as a *Bacillus*, *Streptococcus*, *Streptomyces*, *Staphylococcus*, *Enterococcus*, *Lactobacillus*, *Lactococcus*, *Clostridium*, *Geobacillus*, or *Oceanobacillus* polypeptide having cellulolytic enhancing activity, or a Gram negative bacterial polypeptide such as an *E. coli*, *Pseudomonas*, *Salmonella*, *Campylobacter*, *Helicobacter*, *Flavobacterium*, *Fusobacterium*, *Ilyobacter*, *Neisseria*, or *Ureaplasma* polypeptide having cellulolytic enhancing activity.

In a preferred aspect, the polypeptide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polypeptide having cellulolytic enhancing activity.

In another preferred aspect, the polypeptide is a *Streptococcus equisimilis*, *Streptococcus pyogenes*, *Streptococcus uberis*, or *Streptococcus equi* subsp. *Zooepidemicus* polypeptide having cellulolytic enhancing activity.

In another preferred aspect, the polypeptide is a *Streptomyces achromogenes*, *Streptomyces avermitilis*, *Streptomyces coelicolor*, *Streptomyces griseus*, or *Streptomyces lividans* polypeptide having cellulolytic enhancing activity.

A polypeptide having cellulolytic enhancing activity of the present invention may also be a fungal polypeptide, and more preferably a yeast polypeptide such as a *Candida*, *Kluyveromyces*, *Pichia*, *Saccharomyces*, *Schizosaccharomyces*, or *Yarrowia* polypeptide having cellulolytic enhancing activity; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide having cellulolytic enhancing activity.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide having cellulolytic enhancing activity.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora* crassa, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide having cellulolytic enhancing activity.

In a more preferred aspect, the polypeptide is a *Penicillium* sp. polypeptide having cellulolytic enhancing activity. In a most preferred aspect, the polypeptide is a *Penicillium* sp. NN051602 polypeptide having cellulolytic enhancing activity, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having cellulolytic enhancing activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having cellulolytic enhancing activity of the present invention.

In a preferred aspect, the nucleotide sequence comprises or consists of SEQ ID NO: 1. In another more preferred aspect, the nucleotide sequence comprises or consists of the sequence contained in plasmid pGEM-T-GH61D23Y4 which is contained in *E. coli* DSM 22882. In another preferred aspect, the nucleotide sequence comprises or consists of the mature polypeptide coding sequence of SEQ ID NO: 1. In another preferred aspect, the nucleotide sequence comprises or consists of nucleotides 76 to 832 of SEQ ID NO: 1. In another more preferred aspect, the nucleotide sequence comprises or consists of the mature polypeptide coding sequence contained in plasmid pGEM-T-GH61 D23Y4 which is contained in *E. coli* DSM 22882. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have cellulolytic enhancing activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Penicillium*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 80%, more preferably at least 85%, even more preferably at least 90%, most preferably at least 95%, and even most preferably at least 96%, at least 97%, at least 98%, or at least 99%, which encode a polypeptide having cellulolytic enhancing activity.

Modification of a nucleotide sequence encoding a polypeptide of the present invention may be necessary for the synthesis of polypeptides substantially similar to the polypeptide.

The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for cellulolytic enhancing activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the stringency conditions are high stringency conditions. In another preferred aspect, the stringency conditions are very high stringency conditions.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained in the mature polypeptide coding sequence of SEQ ID NO: 1, or (iii) a full-length complementary strand of (i) or (ii); and (b) isolating the hybridizing polynucleotide, which encodes a polypeptide having cellulolytic enhancing activity. In a preferred aspect, the stringency conditions are high stringency conditions. In another preferred aspect, the stringency conditions are very high stringency conditions.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (VIIIa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from the gene encoding neutral alpha-amylase in *Aspergillus niger* in which the untranslated leader has been replaced by an untranslated leader from the gene encoding triose phosphate isomerase in *Aspergillus nidulans*); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that encodes a signal peptide linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In a preferred aspect, the signal peptide comprises or consists of amino acids 1 to 25 of SEQ ID NO: 2. In another preferred aspect, the signal peptide coding sequence comprises or consists of nucleotides 1 to 75 of SEQ ID NO: 1.

The control sequence may also be a propeptide coding sequence that encodes a propeptide positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides having cellulolytic enhancing activity. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens, Bacillus lentus, Bacillus licheniformis, Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis, Streptococcus pyogenes, Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes, Streptomyces avermitilis, Streptomyces coelicolor, Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-207, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Chrysosporium, Coprinus, Coriolus, Cryptococcus, Filibasidium, Fusarium, Humicola,*

*Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Penicillium*. In a more preferred aspect, the cell is *Penicillium* sp. NN051602.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

Plants

The present invention also relates to plants, e.g., a transgenic plant, plant part, or plant cell, comprising an isolated polynucleotide encoding a polypeptide having cellulolytic enhancing activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, *Poa*), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more (several) expression constructs encoding a polypeptide of the present invention into the plant host genome or chloroplast genome and propagating the resulting modified plant or plant cell into a transgenic plant or plant cell.

The expression construct is conveniently a nucleic acid construct that comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV, the maize ubiquitin 1, and the rice actin 1 promoter may be used (Franck et al., 1980, *Cell* 21: 285-294; Christensen et al., 1992, *Plant Mol. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards and Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the *chlorella* virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may be inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron that is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods of producing a polypeptide of the present invention comprising: (a) cultivating a transgenic plant or a plant cell comprising a polynucleotide encoding the polypeptide having cellulolytic enhancing activity of the present invention under conditions conducive for production of the polypeptide; and (b) recovering the polypeptide.

In embodiments, in addition to direct transformation of a particular plant genotype with a construct prepared according to the present invention, transgenic plants may be made by crossing a plant having a construct of the present invention to a second plant lacking the construct. For example, a construct encoding a polypeptide having cellulolytic enhancing activity or a portion thereof can be introduced into a particular plant variety by crossing, without the need for ever directly transforming a plant of that given variety. Therefore, the present invention not only encompasses a plant directly regenerated from cells which have been transformed in accordance with the present invention, but also the progeny of such plants. As used herein, progeny may refer to the offspring of any generation of a parent plant prepared in accordance with the present invention. Such progeny may include a DNA construct prepared in accordance with the present invention, or a portion of a DNA construct prepared in accordance with the present invention. In embodiments, crossing results in a transgene of the present invention being introduced into a plant line by cross pollinating a starting line with a donor plant line that includes a transgene of the present invention. Non-limiting examples of such steps are further articulated in U.S. Pat. No. 7,151,204.

It is envisioned that plants including a polypeptide having cellulolytic enhancing activity of the present invention include plants generated through a process of backcross conversion. For examples, plants of the present invention include plants referred to as a backcross converted genotype, line, inbred, or hybrid.

In embodiments, genetic markers may be used to assist in the introgression of one or more transgenes of the invention from one genetic background into another. Marker assisted selection offers advantages relative to conventional breeding in that it can be used to avoid errors caused by phenotypic variations. Further, genetic markers may provide data regarding the relative degree of elite germplasm in the individual progeny of a particular cross. For example, when a plant with a desired trait which otherwise has a non-agronomically desirable genetic background is crossed to an elite parent, genetic markers may be used to select progeny which not only possess the trait of interest, but also have a relatively large proportion of the desired germplasm. In this way, the number of generations required to introgress one or more traits into a particular genetic background is minimized.

Removal or Reduction of Cellulolytic Enhancing Activity

The present invention also relates to methods of producing a mutant of a parent cell, which comprises disrupting or deleting a polynucleotide, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphate, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to methods of producing a native or heterologous polypeptide, comprising: (a) cultivating the mutant cell under conditions conducive for production of the polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein product essentially free of cellulolytic enhancing activity by fermentation of a cell that produces both a polypeptide of the present invention as well as the protein product of interest by adding an effective amount of an agent capable of inhibiting cellulolytic enhancing activity to the fermentation broth before, during, or after the fermentation has been completed, recovering the product of interest from the fermentation broth, and optionally subjecting the recovered product to further purification.

In a further aspect, the present invention relates to a method of producing a protein product essentially free of cellulolytic enhancing activity by cultivating the cell under conditions permitting the expression of the product, subjecting the resultant culture broth to a combined pH and temperature treatment so as to reduce the cellulolytic enhancing activity substantially, and recovering the product from the culture broth. Alternatively, the combined pH and temperature treatment may be performed on an enzyme preparation recovered from the culture broth. The combined pH and temperature treatment may optionally be used in combination with a treatment with an cellulolytic enhancing inhibitor.

In accordance with this aspect of the invention, it is possible to remove at least 60%, preferably at least 75%, more preferably at least 85%, still more preferably at least 95%, and most preferably at least 99% of the cellulolytic enhancing activity. Complete removal of cellulolytic enhancing activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially cellulolytic enhancing-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulolytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The cellulolytic enhancing-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from cellulolytic enhancing activity that is produced by a method of the present invention.

Methods of Inhibiting Expression of a Polypeptide Having Cellulolytic Enhancing Activity The present invention also relates to methods of inhibiting the expression of a polypeptide having cellulolytic enhancing activity in a cell, comprising administering to the cell or expressing in the cell a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (sRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

The dsRNAs of the present invention can be used in gene-silencing. In one aspect, the invention provides methods to selectively degrade RNA using the dsRNAis of the present invention. The process may be practiced in vitro, ex vivo or in vivo. In one aspect, the dsRNA molecules can be used to generate a loss-of-function mutation in a cell, an organ or an animal. Methods for making and using dsRNA molecules to selectively degrade RNA are well known in the art, see, for example, U.S. Pat. Nos. 6,506,559; 6,511,824; 6,515,109; and 6,489,127.

Compositions

The present invention also relates to compositions comprising a polypeptide of the present invention. Preferably, the compositions are enriched in such a polypeptide. The term "enriched" indicates that the cellulolytic enhancing activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum,*

*Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride.*

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Processing of Cellulosic Material

The present invention also relates to methods for degrading or converting a cellulosic material, comprising: treating the cellulosic material with an enzyme composition in the presence of a polypeptide having cellulolytic enhancing activity of the present invention. In a preferred aspect, the method further comprises recovering the degraded or converted cellulosic material.

The present invention also relates to methods of producing a fermentation product, comprising: (a) saccharifying a cellulosic material with an enzyme composition in the presence of a polypeptide having cellulolytic enhancing activity of the present invention; (b) fermenting the saccharified cellulosic material with one or more (several) fermenting microorganisms to produce the fermentation product; and (c) recovering the fermentation product from the fermentation.

The present invention also relates to methods of fermenting a cellulosic material, comprising: fermenting the cellulosic material with one or more (several) fermenting microorganisms, wherein the cellulosic material is saccharified with an enzyme composition in the presence of a polypeptide having cellulolytic enhancing activity of the present invention. In a preferred aspect, the fermenting of the cellulosic material produces a fermentation product. In another preferred aspect, the method further comprises recovering the fermentation product from the fermentation.

The polypeptide having cellulolytic enhancing activity can be in the form of a crude fermentation broth with or without the cells removed or in the form of a semi-purified or purified enzyme preparation or the composition can comprise a host cell of the present invention as a source of the polypeptide having cellulolytic enhancing activity in a fermentation process with the biomass.

The methods of the present invention can be used to saccharify a cellulosic material to fermentable sugars and convert the fermentable sugars to many useful substances, e.g., chemicals and fuels. The production of a desired fermentation product from cellulosic material typically involves pretreatment, enzymatic hydrolysis (saccharification), and fermentation.

The processing of cellulosic material according to the present invention can be accomplished using processes conventional in the art. Moreover, the methods of the present invention can be implemented using any conventional biomass processing apparatus configured to operate in accordance with the invention.

Hydrolysis (saccharification) and fermentation, separate or simultaneous, include, but are not limited to, separate hydrolysis and fermentation (SHF); simultaneous saccharification and fermentation (SSF); simultaneous saccharification and cofermentation (SSCF); hybrid hydrolysis and fermentation (HHF); separate hydrolysis and co-fermentation (SHCF), hybrid hydrolysis and fermentation (HHCF), and direct microbial conversion (DMC). SHF uses separate process steps to first enzymatically hydrolyze lignocellulose to fermentable sugars, e.g., glucose, cellobiose, cellotriose, and pentose sugars, and then ferment the fermentable sugars to ethanol. In SSF, the enzymatic hydrolysis of lignocellulose and the fermentation of sugars to ethanol are combined in one step (Philippidis, G. P., 1996, Cellulose bioconversion technology, in *Handbook on Bioethanol: Production and Utilization*, Wyman, C. E., ed., Taylor & Francis, Washington, D.C., 179-212). SSCF involves the cofermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, lignocellulose hydrolysis, and fermentation) in one or more steps where the same organism is used to produce the enzymes for conversion of the lignocellulose to fermentable sugars and to convert the fermentable sugars into a final product (Lynd, L. R., Weimer, P. J., van Zyl, W. H., and Pretorius, I. S., 2002, Microbial cellulose utilization: Fundamentals and biotechnology, *Microbiol. Mol. Biol. Reviews* 66: 506-577). It is understood herein that any method known in the art comprising pretreatment, enzymatic hydrolysis (saccharification), fermentation, or a combination thereof can be used in the practicing the methods of the present invention.

A conventional apparatus can include a fed-batch stirred reactor, a batch stirred reactor, a continuous flow stirred reactor with ultrafiltration, and/or a continuous plug-flow column reactor (Fernanda de Castilhos Corazza, Flavio Faria de Moraes, Gisella Maria Zanin and Ivo Neitzel, 2003, Optimal control in fed-batch reactor for the cellobiose hydrolysis, *Acta Scientiarum. Technology* 25: 33-38; Gusakov, A. V., and Sinitsyn, A. P., 1985, Kinetics of the enzymatic hydrolysis of cellulose: 1. A mathematical model for a batch reactor process, *Enz. Microb. Technol.* 7: 346-352), an attrition reactor (Ryu, S. K., and Lee, J. M., 1983, Bioconversion of waste cellulose by using an attrition bioreactor, *Biotechnol. Bioeng.* 25: 53-65), or a reactor with intensive stirring induced by an electromagnetic field (Gusakov, A. V., Sinitsyn, A. P., Davydkin, I. Y., Davydkin, V. Y., Protas, O. V., 1996, Enhancement of enzymatic cellulose hydrolysis using a novel type of bioreactor with intensive stirring induced by electromagnetic field, *Appl. Biochem. Biotechnol.* 56: 141-153). Additional reactor types include: Fluidized bed, upflow blanket, immobilized, and extruder type reactors for hydrolysis and/or fermentation.

Pretreatment. In practicing the methods of the present invention, any pretreatment process known in the art can be used to disrupt the plant cell wall components (Chandra et al., 2007, Substrate pretreatment: The key to effective enzymatic hydrolysis of lignocellulosics? *Adv. Biochem. Engin./Biotechnol.* 108: 67-93; Galbe and Zacchi, 2007, Pretreatment of lignocellulosic materials for efficient bioethanol production, *Adv. Biochem. Engin./Biotechnol.* 108: 41-65; Hendriks and Zeeman, 2009, Pretreatments to enhance the digestibility of lignocellulosic biomass, *Bioresource Technol.* 100: 10-18;

Mosier et al., 2005, Features of promising technologies for pretreatment of lignocellulosic biomass, *Bioresource Technol.* 96: 673-686; Taherzadeh and Karimi, 2008, Pretreatment of lignocellulosic wastes to improve ethanol and biogas production: A review, *Int. J. of Mol. Sci.* 9: 1621-1651; Yang and Wyman, 2008, Pretreatment: the key to unlocking low-cost cellulosic ethanol, *Biofuels Bioproducts and Biorefining-Biofpr.* 2: 26-40).

The cellulosic material can also be subjected to particle size reduction, pre-soaking, wetting, washing, or conditioning prior to pretreatment using methods known in the art. Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, and gamma irradiation pretreatments.

The cellulosic material can be pretreated before hydrolysis and/or fermentation. Pretreatment is preferably performed prior to the hydrolysis. Alternatively, the pretreatment can be carried out simultaneously with hydrolysis, such as simultaneously with treatment of the cellulosic material with an enzyme composition of the present invention to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic material is heated to disrupt the plant cell wall components, including lignin, hemicellulose, and cellulose to make the cellulose and other fractions, e.g., hemicellulase, accessible to enzymes. The lignocellulose material is passed to or through a reaction vessel where steam is injected to increase the temperature to the required temperature and pressure and is retained therein for the desired reaction time. Steam pretreatment is preferably done at 140-230° C., more preferably 160-200° C., and most preferably 170-190° C., where the optimal temperature range depends on any addition of a chemical catalyst. Residence time for the steam pretreatment is preferably 1-15 minutes, more preferably 3-12 minutes, and most preferably 4-10 minutes, where the optimal residence time depends on temperature range and any addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 20020164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

A catalyst such as $H_2SO_4$ or $SO_2$ (typically 0.3 to 3% w/w) is often added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762).

Chemical Pretreatment: The term "chemical treatment" refers to any chemical pretreatment that promotes the separation and/or release of cellulose, hemicellulose, and/or lignin. Examples of suitable chemical pretreatment processes include, for example, dilute acid pretreatment, lime pretreatment, wet oxidation, ammonia fiber/freeze explosion (AFEX), ammonia percolation (APR), and organosolv pretreatments.

In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment can be performed with a number of reactor designs, e.g., plug-flow reactors, counter-current reactors, or continuous counter-current shrinking bed reactors (Duff and Murray, 1996, supra; Schell et al., 2004, *Bioresource Technol.* 91: 179-188; Lee et al., 1999, *Adv. Biochem. Eng. Biotechnol.* 65: 93-115).

Several methods of pretreatment under alkaline conditions can also be used. These alkaline pretreatments include, but are not limited to, lime pretreatment, wet oxidation, ammonia percolation (APR), and ammonia fiber/freeze explosion (AFEX).

Lime pretreatment is performed with calcium carbonate, sodium hydroxide, or ammonia at low temperatures of 85-150° C. and residence times from 1 hour to several days (Wyman et al., 2005, *Bioresource Technol.* 96: 1959-1966; Mosier et al., 2005, *Bioresource Technol.* 96: 673-686). WO 2006/110891, WO 2006/11899, WO 2006/11900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technol.* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed at preferably 1-40% dry matter, more preferably 2-30% dry matter, and most preferably 5-20% dry matter, and often the initial pH is increased by the addition of alkali such as sodium carbonate.

A modification of the wet oxidation pretreatment method, known as wet explosion (combination of wet oxidation and steam explosion), can handle dry matter up to 30%. In wet explosion, the oxidizing agent is introduced during pretreatment after a certain residence time. The pretreatment is then ended by flashing to atmospheric pressure (WO 2006/032282).

Ammonia fiber explosion (AFEX) involves treating cellulosic material with liquid or gaseous ammonia at moderate temperatures such as 90-100° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121:1133-1141; Teymouri et al., 2005, *Bioresource Technol.* 96: 2014-2018). AFEX pretreatment results in the depolymerization of cellulose and partial hydrolysis of hemicellulose. Lignin-carbohydrate complexes are cleaved.

Organosolv pretreatment delignifies cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121:219-230). Sulphuric acid is usually added as a catalyst. In organosolv pretreatment, the majority of the hemicellulose is removed.

Other examples of suitable pretreatment methods are described by Schell et al., 2003, *Appl. Biochem. and Biotechnol. Vol.* 105-108, p. 69-85, and Mosier et al., 2005, *Bioresource Technology* 96: 673-686, and U.S. Published Application 2002/0164730.

In one aspect, the chemical pretreatment is preferably carried out as an acid treatment, and more preferably as a continuous dilute and/or mild acid treatment. The acid is typically sulfuric acid, but other acids can also be used, such as acetic acid, citric acid, nitric acid, phosphoric acid, tartaric acid, succinic acid, hydrogen chloride or mixtures thereof. Mild acid treatment is conducted in the pH range of preferably 1-5, more preferably 1-4, and most preferably 1-3. In one aspect, the acid concentration is in the range from preferably 0.01 to 20 wt % acid, more preferably 0.05 to 10 wt % acid, even more preferably 0.1 to 5 wt % acid, and most preferably 0.2 to 2.0 wt % acid. The acid is contacted with the cellulosic material and held at a temperature in the range of preferably 160-220° C., and more preferably 165-195° C., for periods ranging from seconds to minutes to, e.g., 1 second to 60 minutes.

In another aspect, pretreatment is carried out as an ammonia fiber explosion step (AFEX pretreatment step).

In another aspect, pretreatment takes place in an aqueous slurry. In preferred aspects, the cellulosic material is present during pretreatment in amounts preferably between 10-80 wt %, more preferably between 20-70 wt %, and most preferably between 30-60 wt %, such as around 50 wt %. The pretreated cellulosic material can be unwashed or washed using any method known in the art, e.g., washed with water.

Mechanical Pretreatment: The term "mechanical pretreatment" refers to various types of grinding or milling (e.g., dry milling, wet milling, or vibratory ball milling).

Physical Pretreatment: The term "physical pretreatment" refers to any pretreatment that promotes the separation and/or release of cellulose, hemicellulose, and/or lignin from cellulosic material. For example, physical pretreatment can involve irradiation (e.g., microwave irradiation), steaming/steam explosion, hydrothermolysis, and combinations thereof.

Physical pretreatment can involve high pressure and/or high temperature (steam explosion). In one aspect, high pressure means pressure in the range of preferably about 300 to about 600 psi, more preferably about 350 to about 550 psi, and most preferably about 400 to about 500 psi, such as around 450 psi. In another aspect, high temperature means temperatures in the range of about 100 to about 300° C., preferably about 140 to about 235° C. In a preferred aspect, mechanical pretreatment is performed in a batch-process, steam gun hydrolyzer system that uses high pressure and high temperature as defined above, e.g., a Sunds Hydrolyzer available from Sunds Defibrator AB, Sweden.

Combined Physical and Chemical Pretreatment: The cellulosic material can be pretreated both physically and chemically. For instance, the pretreatment step can involve dilute or mild acid treatment and high temperature and/or pressure treatment. The physical and chemical pretreatments can be carried out sequentially or simultaneously, as desired. A mechanical pretreatment can also be included.

Accordingly, in a preferred aspect, the cellulosic material is subjected to mechanical, chemical, or physical pretreatment, or any combination thereof to promote the separation and/or release of cellulose, hemicellulose and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques can involve applying lignin-solubilizing microorganisms (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, Physicochemical and biological treatments for enzymatic/microbial conversion of cellulosic biomass, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, Fermentation of lignocellulosic hydrolysates for ethanol production, *Enz. Microb. Tech.* 18: 312-331; and Vallander and Eriksson, 1990, Production of ethanol from lignocellulosic materials: State of the art, *Adv. Biochem. Eng./Biotechnol.* 42: 63-95).

Saccharification. In the hydrolysis step, also known as saccharification, the cellulosic material, e.g., pretreated, is hydrolyzed to break down cellulose and alternatively also hemicellulose to fermentable sugars, such as glucose, cellobiose, xylose, xylulose, arabinose, mannose, galactose, or soluble oligosaccharides. The hydrolysis is performed enzymatically by an enzyme composition in the presence of a polypeptide having cellulolytic enhancing activity of the present invention. The composition can further comprise one or more hemicellulolytic enzymes. The enzymes of the compositions can also be added sequentially.

Enzymatic hydrolysis is preferably carried out in a suitable aqueous environment under conditions that can be readily determined by one skilled in the art. In a preferred aspect, hydrolysis is performed under conditions suitable for the activity of the enzyme(s), i.e., optimal for the enzyme(s). The hydrolysis can be carried out as a fed batch or continuous process where the pretreated cellulosic material (substrate) is fed gradually to, for example, an enzyme containing hydrolysis solution.

The saccharification is generally performed in stirred-tank reactors or fermentors under controlled pH, temperature, and mixing conditions. Suitable process time, temperature and pH conditions can readily be determined by one skilled in the art. For example, the saccharification can last up to 200 hours, but is typically performed for preferably about 12 to about 168 hours, more preferably about 24 to about 120 hours, and most preferably about 48 to about 72 hours. The temperature is in the range of preferably about 40° C. to about 70° C., more preferably about 45° C. to about 65° C., and more preferably about 50° C. to about 60° C., in particular about 55° C. The pH is in the range of preferably about 3 to about 9, more preferably about 3.5 to about 8, more preferably about 4 to about 7, and most preferably about 4.5 to about 6, in particular about pH 5. The dry solids content is in the range of preferably about 1 to about 50 wt %, more preferably about 5 to about 40 wt %, more preferably about 10 to about 30 wt %, and most preferably about 15 to about 25 wt %.

In addition to a polypeptide having cellulolytic enhancing activity of the present invention, the cellulolytic enzyme components of the composition are preferably enzymes having endoglucanase, cellobiohydrolase, and beta-glucosidase activities. In a preferred aspect, the enzyme composition comprises one or more (several) cellulolytic enzymes selected from the group consisting of a cellulase, an endoglucanase, a cellobiohydrolase, and a beta-glucosidase. In another preferred aspect, the cellulolytic enzyme preparation further or even further comprises one or more additional enzyme activities selected from the group consisting of hemicellulases, esterases (e.g., lipases, phospholipases, and/or cutinases), proteases, laccases, peroxidases, or mixtures thereof. In the methods of the present invention, the additional enzyme(s) can be added prior to or during fermentation, including during or after propagation of the fermenting microorganism(s).

The enzymes can be derived or obtained from any suitable origin, including, bacterial, fungal, yeast, plant, or mammalian origin. The term "obtained" means herein that the enzyme may have been isolated from an organism that naturally produces the enzyme as a native enzyme. The term "obtained" also means herein that the enzyme may have been produced recombinantly in a host organism employing methods described herein, wherein the recombinantly produced enzyme is either native or foreign to the host organism or has a modified amino acid sequence, e.g., having one or more amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained recombinantly, such as by site-directed mutagenesis or shuffling.

The enzymes used in the present invention can be in any form suitable for use in the methods described herein, such as a crude fermentation broth with or without cells or substantially pure polypeptides. The enzyme(s) can be a dry powder or granulate, a liquid, a stabilized liquid, or a protected enzyme(s). Liquid enzyme preparations can, for instance, be stabilized by adding stabilizers such as a sugar, a sugar alcohol or another polyol, and/or lactic acid or another organic acid according to established process.

The optimum amounts of the enzymes and polypeptides having cellulolytic enhancing activity depend on several factors including, but not limited to, the mixture of component cellulolytic enzymes, the cellulosic substrate, the concentration of cellulosic substrate, the pretreatment(s) of the cellulosic substrate, temperature, time, pH, and inclusion of fermenting organism (e.g., yeast for Simultaneous Saccharification and Fermentation).

In a preferred aspect, an effective amount of cellulolytic enzyme(s) to cellulosic material is about 0.5 to about 50 mg, preferably at about 0.5 to about 40 mg, more preferably at about 0.5 to about 25 mg, more preferably at about 0.75 to about 20 mg, more preferably at about 0.75 to about 15 mg, even more preferably at about 0.5 to about 10 mg, and most preferably at about 2.5 to about 10 mg per g of cellulosic material.

In another preferred aspect, an effective amount of polypeptide(s) having cellulolytic enhancing activity to cellulosic material is about 0.01 to about 50.0 mg, preferably about 0.01 to about 40 mg, more preferably about 0.01 to about 30 mg, more preferably about 0.01 to about 20 mg, more preferably about 0.01 to about 10 mg, more preferably about 0.01 to about 5 mg, more preferably at about 0.025 to about 1.5 mg, more preferably at about 0.05 to about 1.25 mg, more preferably at about 0.075 to about 1.25 mg, more preferably at about 0.1 to about 1.25 mg, even more preferably at about 0.15 to about 1.25 mg, and most preferably at about 0.25 to about 1.0 mg per g of cellulosic material.

In another preferred aspect, an effective amount of polypeptide(s) having cellulolytic enhancing activity to cellulolytic enzyme(s) is about 0.005 to about 1.0 g, preferably at about 0.01 to about 1.0 g, more preferably at about 0.15 to about 0.75 g, more preferably at about 0.15 to about 0.5 g, more preferably at about 0.1 to about 0.5 g, even more preferably at about 0.1 to about 0.5 g, and most preferably at about 0.05 to about 0.2 g per g of cellulolytic enzyme(s).

In the methods of the present invention, the enzyme composition may comprise any protein involved in the processing of a cellulose-containing material to glucose, or hemicellulose to xylose, mannose, galactose, and arabinose, their polymers, or products derived from them as described below. In one aspect, the enzyme composition comprises one or more enzymes selected from the group consisting of an endoglucanase, a cellobiohydrolase, and a beta-glucosidase. In another aspect, the enzyme composition further or even further comprises one or more additional enzyme activities to improve the degradation of the cellulose-containing material. Preferred additional enzymes are xylanases, hemicellulases, esterases (e.g., lipases, phospholipases, and/or cutinases), proteases, laccases, peroxidases, or mixtures thereof.

The enzyme composition may be a monocomponent preparation, e.g., an endoglucanase, a multicomponent preparation, e.g., endoglucanase, cellobiohydrolase, beta-glucosidase, or a combination of multicomponent and monocomponent protein preparations. The cellulolytic proteins may have activity, i.e., hydrolyze cellulose, either in the acid, neutral, or alkaline pH range.

One or more components of the enzyme composition may be a recombinant component, i.e., produced by cloning of a DNA sequence encoding the single component and subsequent cell transformed with the DNA sequence and expressed in a host (see, for example, WO 91/17243 and WO 91/17244). The host is preferably a heterologous host (enzyme is foreign to host), but the host may under certain conditions also be a homologous host (enzyme is native to host). Monocomponent cellulolytic proteins may also be prepared by purifying such a protein from a fermentation broth.

The enzymes used in the present invention may be in any form suitable for use in the processes described herein, such as, for example, a crude fermentation broth with or without cells, a dry powder or granulate, a liquid, a stabilized liquid, or a protected enzyme. Liquid enzyme preparations may, for instance, be stabilized by adding stabilizers such as a sugar, a sugar alcohol or another polyol, and/or lactic acid or another organic acid according to established process.

A polypeptide having cellulolytic enzyme activity may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus*, or *Oceanobacillus* polypeptide having cellulolytic enzyme activity, or a Gram negative bacterial polypeptide such as an *E. coli, Pseudomonas, Salmonella, Campylobacter, Helicobacter, Flavobacterium, Fusobacterium, Ilyobacter, Neisseria*, or *Ureaplasma* polypeptide having cellulolytic enzyme activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, or *Bacillus thuringiensis* polypeptide having cellulolytic enzyme activity.

In another preferred aspect, the polypeptide is a *Streptococcus equisimilis, Streptococcus pyogenes, Streptococcus uberis*, or *Streptococcus equi* subsp. *Zooepidemicus* polypeptide having cellulolytic enzyme activity.

In another preferred aspect, the polypeptide is a *Streptomyces achromogenes, Streptomyces avermitilis, Streptomyces coelicolor, Streptomyces griseus*, or *Streptomyces lividans* polypeptide having cellulolytic enzyme activity.

The polypeptide having cellulolytic enzyme activity may also be a fungal polypeptide, and more preferably a yeast polypeptide such as a *Candida, Kluyveromyces, Pichia, Saccharomyces, Schizosaccharomyces*, or *Yarrowia* polypeptide having cellulolytic enzyme activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* polypeptide having cellulolytic enzyme activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having cellulolytic enzyme activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei, Trichoderma viride*, or *Trichophaea saccata* polypeptide having cellulolytic enzyme activity.

Chemically modified or protein engineered mutants of cellulolytic proteins may also be used.

Examples of commercial cellulolytic protein preparations suitable for use in the present invention include, for example, CELLIC™ Ctec (Novozymes NS), CELLUCLAST™ (Novozymes NS), and NOVOZYM™ 188 (Novozymes NS). Other commercially available preparations comprising cellulase that may be used include CELLUZYME™, CEREFLO™ and ULTRAFLO™ (Novozymes NS), LAMINEX™ and SPEZYME™ CP (Genencor Int.), ROHAMENT™ 7069 W (Röhm GmbH), and FIBREZYME® LDI, FIBREZYME® LBR, or VISCOSTAR® 150L (Dyadic International, Inc., Jupiter, Fla., USA). The cellulase enzymes are added in amounts effective from about 0.001% to about 5.0% wt. of solids, more preferably from about 0.025% to about 4.0% wt. of solids, and most preferably from about 0.005% to about 2.0% wt. of solids.

Examples of bacterial endoglucanases that can be used in the methods of the present invention, include, but are not limited to, an *Acidothermus cellulolyticus* endoglucanase (WO 91/05039; WO 93/15186; U.S. Pat. No. 5,275,944; WO 96/02551; U.S. Pat. No. 5,536,655, WO 00/70031, WO 05/093050); *Thermobifida fusca* endoglucanase III (WO 05/093050); and *Thermobifida fusca* endoglucanase V (WO 05/093050).

Examples of fungal endoglucanases that can be used in the methods of the present invention, include, but are not limited to, a *Trichoderma reesei* endoglucanase I (Penttila et al., 1986, *Gene* 45: 253-263; GENBANK™ accession no. M15665); *Trichoderma reesei* endoglucanase II (Saloheimo, et al., 1988, *Gene* 63:11-22; GENBANK™ accession no. M19373); *Trichoderma reesei* endoglucanase III (Okada et al., 1988, *Appl. Environ. Microbiol.* 64: 555-563; GENBANK™ accession no. AB003694); *Trichoderma reesei* endoglucanase IV (Saloheimo et al., 1997, *Eur. J. Biochem.* 249: 584-591; GENBANK™ accession no. Y11113); and *Trichoderma reesei* endoglucanase V (Saloheimo et al., 1994, *Molecular Microbiology* 13: 219-228; GENBANK™ accession no. Z33381); *Aspergillus aculeatus* endoglucanase (Ooi et al., 1990, *Nucleic Acids Research* 18: 5884); *Aspergillus kawachii* endoglucanase (Sakamoto et al., 1995, *Current Genetics* 27: 435-439); *Erwinia carotovara* endoglucanase (Saarilahti et al., 1990, *Gene* 90: 9-14); *Fusarium oxysporum* endoglucanase (GENBANK™ accession no. L29381); *Humicola grisea* var. *thermoidea* endoglucanase (GENBANK™ accession no. AB003107); *Melanocarpus albomyces* endoglucanase (GENBANK™ accession no. MAL515703); *Neurospora crassa* endoglucanase (GENBANK™ accession no. XM_324477); *Humicola insolens* endoglucanase V; *Myceliophthora thermophila* CBS 117.65 endoglucanase; basidiomycete CBS 495.95 endoglucanase; basidiomycete CBS 494.95 endoglucanase; *Thielavia terrestris* NRRL 8126 CEL6B endoglucanase; *Thielavia terrestris* NRRL 8126 CEL6C endoglucanase); *Thielavia terrestris* NRRL 8126 CEL7C endoglucanase; *Thielavia terrestris* NRRL 8126 CEL7E endoglucanase; *Thielavia terrestris* NRRL 8126 CEL7F endoglucanase; *Cladorrhinum foecundissimum* ATCC 62373 CEL7A endoglucanase; and *Trichoderma reesei* strain No. VTT-D-80133 endoglucanase (GENBANK™ accession no. M15665).

Examples of cellobiohydrolases useful in the methods of the present invention include, but are not limited to, *Trichoderma reesei* cellobiohydrolase I; *Trichoderma reesei* cellobiohydrolase II; *Humicola insolens* cellobiohydrolase I, *Myceliophthora thermophila* cellobiohydrolase II, *Thielavia terrestris* cellobiohydrolase II (CEL6A), *Chaetomium thermophilum* cellobiohydrolase I, and *Chaetomium thermophilum* cellobiohydrolase II.

Examples of beta-glucosidases useful in the methods of the present invention include, but are not limited to, *Aspergillus oryzae* beta-glucosidase; *Aspergillus fumigatus* beta-glucosidase; *Penicillium brasilianum* IBT 20888 beta-glucosidase; *Aspergillus niger* beta-glucosidase; and *Aspergillus aculeatus* beta-glucosidase.

The *Aspergillus oryzae* polypeptide having beta-glucosidase activity can be obtained according to WO 2002/095014. The *Aspergillus fumigatus* polypeptide having beta-glucosidase activity can be obtained according to WO 2005/047499.

The *Penicillium brasilianum* polypeptide having beta-glucosidase activity can be obtained according to WO 2007/019442. The *Aspergillus niger* polypeptide having beta-glucosidase activity can be obtained according to Dan et al., 2000, *J. Biol. Chem.* 275: 4973-4980. The *Aspergillus aculeatus* polypeptide having beta-glucosidase activity can be obtained according to Kawaguchi et al., 1996, *Gene* 173: 287-288.

The beta-glucosidase may be a fusion protein. In one aspect, the beta-glucosidase is the *Aspergillus oryzae* beta-glucosidase variant BG fusion protein or the *Aspergillus oryzae* beta-glucosidase fusion protein obtained according to WO 2008/057637.

Other endoglucanases, cellobiohydrolases, and beta-glucosidases are disclosed in numerous Glycosyl Hydrolase families using the classification according to Henrissat B., 1991, A classification of glycosyl hydrolases based on amino-acid sequence similarities, *Biochem. J.* 280: 309-316, and Henrissat B., and Bairoch A., 1996, Updating the sequence-based classification of glycosyl hydrolases, *Biochem. J.* 316: 695-696.

Other cellulolytic enzymes that may be used in the present invention are described in EP 495,257, EP 531,315, EP 531, 372, WO 89/09259, WO 94/07998, WO 95/24471, WO 96/11262, WO 96/29397, WO 96/034108, WO 97/14804, WO 98/08940, WO 98/012307, WO 98/13465, WO 98/015619, WO 98/015633, WO 98/028411, WO 99/06574, WO 99/10481, WO 99/025846, WO 99/025847, WO 99/031255, WO 2000/009707, WO 2002/050245, WO 2002/076792, WO 2002/101078, WO 2003/027306, WO 2003/052054, WO 2003/052055, WO 2003/052056, WO 2003/052057, WO 2003/052118, WO 2004/016760, WO 2004/043980, WO 2004/048592, WO 2005/001065, WO 2005/028636, WO 2005/093050, WO 2005/093073, WO 2006/074005, WO 2006/117432, WO 2007/071818, WO 2007/071820, WO 2008/008070, WO 2008/008793, U.S. Pat. Nos. 4,435,307, 5,457,046, 5,648, 263, 5,686,593, 5,691,178, 5,763,254, and 5,776,757.

Examples of commercial xylan degrading enzyme preparations suitable for use in the present invention include, for example, SHEARZYME™ (Novozymes NS), CELLIC™ Htec (Novozymes A/S), VISCOZYME® (Novozymes A/S), ULTRAFLO® (Novozymes A/S), PULPZYME® HC (Novozymes A/S), MULTIFECT® Xylanase (Genencor), ECOPULP® TX-200A (AB Enzymes), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK).

Examples of xylanases useful in the methods of the present invention include, but are not limited to, *Aspergillus aculeatus* xylanase (GeneSeqP:AAR63790; WO 94/21785), *Aspergillus fumigatus* xylanases (WO 2006/078256), and *Thielavia terrestris* NRRL 8126 xylanases (WO 2009/079210).

Examples of beta-xylosidases useful in the methods of the present invention include, but are not limited to, *Trichoderma reesei* beta-xylosidase (UniProtKB/TrEMBL accession number Q92458), *Talaromyces emersonii* (SwissProt accession number Q8x212), and *Neurospora crassa* (SwissProt accession number Q7SOW4).

Examples of acetylxylan esterases useful in the methods of the present invention include, but are not limited to, *Hypocrea jecorina* acetylxylan esterase (WO 2005/001036), *Neurospora crassa* acetylxylan esterase (UniProt accession number q7s259), *Thielavia terrestris* NRRL 8126 acetylxylan esterase (WO 2009/042846), *Chaetomium globosum* acetylxylan esterase (Uniprot accession number Q2GWX4), *Chaetomium gracile* acetylxylan esterase (GeneSeqP accession number AAB82124), *Phaeosphaeria nodorum* acetylxylan esterase (Uniprot accession number QOUHJ1), and *Humicola insolens* DSM 1800 acetylxylan esterase (WO 2009/073709).

Examples of ferulic acid esterases useful in the methods of the present invention include, but are not limited to, *Humicola insolens* DSM 1800 feruloyl esterase (WO 2009/076122), *Neurospora crassa* feruloyl esterase (UniProt accession number Q9HGR3), and *Neosartorya fischeri* feruloyl esterase (UniProt Accession number A1D9T4).

Examples of arabinofuranosidases useful in the methods of the present invention include, but are not limited to, *Humicola insolens* DSM 1800 arabinofuranosidase (WO 2009/073383) and *Aspergillus niger* arabinofuranosidase (GeneSeqP accession number AAR94170).

Examples of alpha-glucuronidases useful in the methods of the present invention include, but are not limited to, *Aspergillus clavatus* alpha-glucuronidase (UniProt accession number alccl2), *Trichoderma reesei* alpha-glucuronidase (Uniprot accession number Q99024), *Talaromyces emersonii* alpha-glucuronidase (UniProt accession number Q8X211), *Aspergillus niger* alpha-glucuronidase (Uniprot accession number Q96WX9), *Aspergillus terreus* alpha-glucuronidase (SwissProt accession number QOCJP9), and *Aspergillus fumigatus* alpha-glucuronidase (SwissProt accession number Q4WW45).

The cellulolytic enzymes and proteins used in the methods of the present invention may be produced by fermentation of the above-noted microbial strains on a nutrient medium containing suitable carbon and nitrogen sources and inorganic salts, using procedures known in the art (see, e.g., Bennett, J. W. and LaSure, L. (eds.), *More Gene Manipulations in Fungi*, Academic Press, CA, 1991). Suitable media are available from commercial suppliers or may be prepared according to published compositions (e.g., in catalogues of the American Type Culture Collection). Temperature ranges and other conditions suitable for growth and cellulolytic enzyme production are known in the art (see, e.g., Bailey, J. E., and Ollis, D. F., *Biochemical Engineering Fundamentals*, McGraw-Hill Book Company, NY, 1986).

The fermentation can be any method of cultivation of a cell resulting in the expression or isolation of a cellulolytic enzyme. Fermentation may, therefore, be understood as comprising shake flask cultivation, or small- or large-scale fermentation (including continuous, batch, fed-batch, or solid state fermentations) in laboratory or industrial fermentors performed in a suitable medium and under conditions allowing the cellulolytic enzyme to be expressed or isolated. The resulting cellulolytic enzymes produced by the methods described above may be recovered from the fermentation medium and purified by conventional procedures.

Fermentation. The fermentable sugars obtained from the pretreated and hydrolyzed cellulosic material can be fermented by one or more fermenting microorganisms capable of fermenting the sugars directly or indirectly into a desired fermentation product. "Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and can easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation can be separate or simultaneous. Such methods include, but are not limited to, separate hydrolysis and fermentation (SHF); simultaneous saccharification and fermentation (SSF); simultaneous saccharification and cofermentation (SSCF); hybrid hydrolysis and fermentation (HHF); SHCF (separate hydrolysis and co-fermentation), HHCF (hybrid hydrolysis and fermentation), and direct microbial conversion (DMC).

Any suitable hydrolyzed cellulosic material can be used in the fermentation step in practicing the present invention. The material is generally selected based on the desired fermentation product, i.e., the substance to be obtained from the fermentation, and the process employed, as is well known in the art. Examples of substrates suitable for use in the methods of present invention, include cellulosic materials, such as wood or plant residues or low molecular sugars DP1-3 obtained from processed cellulosic material that can be metabolized by the fermenting microorganism, and which can be supplied by direct addition to the fermentation medium.

The term "fermentation medium" is understood herein to refer to a medium before the fermenting microorganism(s) is(are) added, such as, a medium resulting from a saccharification process, as well as a medium used in a simultaneous saccharification and fermentation process (SSF).

"Fermenting microorganism" refers to any microorganism, including bacterial and fungal organisms, suitable for use in a desired fermentation process to produce a fermentation product. The fermenting organism can be $C_6$ and/or $C_5$ fermenting organisms, or a combination thereof. Both $C_6$ and $C_5$ fermenting organisms are well known in the art. Suitable fermenting microorganisms are able to ferment, i.e., convert, sugars, such as glucose, xylose, xylulose, arabinose, maltose, mannose, galactose, or oligosaccharides, directly or indirectly into the desired fermentation product.

Examples of bacterial and fungal fermenting organisms producing ethanol are described by Lin et al., 2006, *Appl. Microbiol. Biotechnol.* 69: 627-642.

Examples of fermenting microorganisms that can ferment C6 sugars include bacterial and fungal organisms, such as yeast. Preferred yeast includes strains of the *Saccharomyces* spp., preferably *Saccharomyces cerevisiae*.

Examples of fermenting organisms that can ferment C5 sugars include bacterial and fungal organisms, such as yeast. Preferred C5 fermenting yeast include strains of *Pichia*, preferably *Pichia stipitis*, such as *Pichia stipitis* CBS 5773; strains of *Candida*, preferably *Candida boidinii, Candida brassicae, Candida sheatae, Candida diddensii, Candida pseudotropicalis*, or *Candida utilis*.

Other fermenting organisms include strains of *Zymomonas*, such as *Zymomonas mobilis; Hansenula*, such as *Hansenula anomala; Kluyveromyces*, such as *K. fragilis; Schizosaccharomyces*, such as *S. pombe*; and *E. coli*, especially *E. coli* strains that have been genetically modified to improve the yield of ethanol.

In a preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*. In another preferred aspect, the yeast is a *Kluyveromyces*. In another more preferred aspect, the yeast is *Kluyveromyces marxianus*. In another more preferred aspect, the yeast is *Kluyveromyces fragilis*. In another preferred aspect, the yeast is a *Candida*. In another more preferred aspect, the yeast is *Candida boidinii*. In another more preferred aspect, the yeast is *Candida brassicae*. In another more preferred aspect, the yeast is *Candida diddensii*. In another more preferred aspect, the yeast is *Candida pseudotropicalis*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Pachysolen*. In another more preferred aspect, the yeast is *Pachysolen tannophilus*. In another more preferred aspect, the yeast is a *Pichia*. In another more preferred aspect, the yeast is a *Pichia stipitis*. In another preferred aspect, the yeast is a *Bretannomyces*. In another more preferred aspect, the yeast is *Bretannomyces clausenii* (Philippidis, G. P., 1996, Cellulose bioconversion technology, in *Handbook on Bioethanol: Production and Utilization*, Wyman, C. E., ed., Taylor & Francis, Washington, D.C., 179-212).

Bacteria that can efficiently ferment hexose and pentose to ethanol include, for example, *Zymomonas mobilis* and *Clostridium thermocellum* (Philippidis, 1996, supra).

In a preferred aspect, the bacterium is a *Zymomonas*. In a more preferred aspect, the bacterium is *Zymomonas mobilis*. In another preferred aspect, the bacterium is a *Clostridium*. In another more preferred aspect, the bacterium is *Clostridium thermocellum*.

Commercially available yeast suitable for ethanol production includes, e.g., ETHANOL RED™ yeast (available from Fermentis/Lesaffre, USA), FALI™ (available from Fleischmann's Yeast, USA), SUPERSTART™ and THERMOSACC™ fresh yeast (available from Ethanol Technology, WI, USA), BIOFERM™ AFT and XR (available from NABC—North American Bioproducts Corporation, GA, USA), GERT STRAND™ (available from Gert Strand AB, Sweden), and FERMIOL™ (available from DSM Specialties).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, Cloning and improving the expression of *Pichia stipitis* xylose reductase gene in *Saccharomyces cerevisiae, Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae, Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli, Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis, Science* 267: 240-243; Deanda et al., 1996, Development of an arabinose-fermenting *Zymomonas mobilis* strain by metabolic pathway engineering, *Appl. Environ. Microbiol.* 62: 4465-4470).

In a preferred aspect, the genetically modified fermenting microorganism is *Saccharomyces cerevisiae*. In another preferred aspect, the genetically modified fermenting microorganism is *Zymomonas mobilis*. In another preferred aspect, the genetically modified fermenting microorganism is *Escherichia coli*. In another preferred aspect, the genetically modified fermenting microorganism is *Klebsiella oxytoca*.

It is well known in the art that the organisms described above can also be used to produce other substances, as described herein.

The fermenting microorganism is typically added to the degraded lignocellulose or hydrolysate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In a preferred aspect, the yeast and/or another microorganism is applied to the degraded lignocellulose or hydrolysate and the fermentation is performed for about 12 to about 96 hours, such as typically 24-60 hours. In a preferred aspect, the temperature is preferably between about 20° C. to about 60° C., more preferably about 25° C. to about 50° C., and most preferably about 32° C. to about 50° C., in particular about 32° C. or 50° C., and the pH is generally from about pH 3 to about pH 7, preferably around pH 4-7. However, some, e.g., bacterial fermenting organisms have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

The most widely used process in the art is the simultaneous saccharification and fermentation (SSF) process where there is no holding stage for the saccharification, meaning that yeast and enzyme are added together.

For ethanol production, following the fermentation the fermented slurry is distilled to extract the ethanol. The ethanol obtained according to the methods of the invention can be used as, e.g., fuel ethanol, drinking ethanol, i.e., potable neutral spirits, or industrial ethanol.

A fermentation stimulator can be used in combination with any of the enzymatic processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products: A fermentation product can be any substance derived from the fermentation. The fermentation product can be, without limitation, an alcohol (e.g., arabinitol, butanol, ethanol, glycerol, methanol, 1,3-propanediol, sorbitol, and xylitol); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); a ketone (e.g., acetone); an amino acid (e.g., aspartic acid, glutamic acid, glycine, lysine, serine, and threonine); and a gas (e.g., methane, hydrogen ($H_2$), carbon dioxide ($CO_2$), and carbon monoxide (CO)). The fermentation product can also be protein as a high value product.

In a preferred aspect, the fermentation product is an alcohol. It will be understood that the term "alcohol" encompasses a substance that contains one or more hydroxyl moieties. In a more preferred aspect, the alcohol is arabinitol. In another more preferred aspect, the alcohol is butanol. In another more preferred aspect, the alcohol is ethanol. In another more preferred aspect, the alcohol is glycerol. In another more preferred aspect, the alcohol is methanol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam, P., and Singh, D., 1995, Processes for fermentative production of xylitol—a sugar substitute, *Process Biochemistry* 30 (2): 117-124; Ezeji, T. C., Qureshi, N. and Blaschek, H. P., 2003, Production of acetone, butanol and ethanol by *Clostridium beijerinckii* BA101 and in situ recovery by gas stripping, *World Journal of Microbiology and Biotechnology* 19 (6): 595-603.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen, R., and Lee, Y. Y., 1997, Membrane-mediated extractive fermentation for lactic acid production from cellulosic biomass, *Appl. Biochem. Biotechnol.* 63-65: 435-448.

In another preferred aspect, the fermentation product is a ketone. It will be understood that the term "ketone" encompasses a substance that contains one or more ketone moieties. In another more preferred aspect, the ketone is acetone. See, for example, Qureshi and Blaschek, 2003, supra.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard, A., and Margaritis, A., 2004, Empirical modeling of batch fermentation kinetics for poly(glutamic acid) production and other microbial biopolymers, *Biotechnology and Bioengineering* 87 (4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, N., A. Miya, and K. Kiriyama, 1997, Studies on hydrogen production by continuous culture system of hydrogen-producing anaerobic bacteria, *Water Science and Technology* 36 (6-7): 41-47; and Gunaseelan V. N. in *Biomass and Bioenergy*, Vol. 13 (1-2), pp. 83-114, 1997, Anaerobic digestion of biomass for methane production: A review.

Recovery. The fermentation product(s) can be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % can be obtained, which can be used as, for example, fuel ethanol, drinking ethanol, i.e., potable neutral spirits, or industrial ethanol.

Detergent Compositions

The polypeptides having cellulolytic enhancing activity of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the invention. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Commercially available cellulases include CELLUZYMET™, and CAREZYME™ (Novozymes A/S), CLAZINASE™, and PURADAX HA™ (Genencor International Inc.), and KAC-500(B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include ALCALASE™ SAVINASE™, PRIMASET™, DURALASE™, ESPERASE™, and KANNASE™ (Novozymes A/S), MAXATASET™, MAXACAL™, MAXAPEM™, PROPERASE™, PURAFECTT™, PURAFECT OXP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include LIPOLASE™ and LIPOLASE ULTRA™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are DURAMYL™, TERMAMYL™, FUNGAMYL™ and BAN™ (Novozymes A/S), RAPIDASE™ and PURASTAR™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include GUARDZYME™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention having cellulolytic enhancing activity may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the invention having cellulolytic enhancing activity may also be incorporated in the detergent formulations disclosed in WO 97/07202, which is hereby incorporated by reference.

Signal Peptide

The present invention also relates to an isolated polynucleotide encoding a signal peptide comprising or consisting of amino acids 1 to 25 of SEQ ID NO: 2. The present invention also relates to nucleic acid constructs comprising a gene encoding a protein, wherein the gene is operably linked to such a polynucleotide encoding a signal peptide comprising or consisting of amino acids 1 to 25 of SEQ ID NO: 2, wherein the gene is foreign to the polynucleotide.

In a preferred aspect, the polynucleotide sequence comprises or consists of nucleotides 1 to 75 of SEQ ID NO: 1.

The present invention also relates to recombinant expression vectors and recombinant host cells comprising such nucleic acid constructs.

The present invention also relates to methods of producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides that comprise a combination of partial or complete polypeptide sequences obtained from at least two different proteins wherein one or more (several) may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples that should not be construed as limiting the scope of the invention.

EXAMPLES

Strain

*Penicillium* sp. NN051602 was used as the source of the GH61 polypeptide having cellulolytic enhancing activity. *Aspergillus oryzae* strain HowB101 (WO 95/35385) was used as a host for recombinantly expressing the *Penicillium* sp. GH61 polypeptide having cellulolytic enhancing activity.

Media

PDA plates were composed of 39 grams of potato dextrose agar and deionized water to 1 liter.

NNCYP-PCS medium was composed per liter of 5.0 g of NaNO$_3$, 3.0 g of NH$_4$Cl, 2.0 g of MES, 2.5 g of citric acid, 0.2 g of CaCl$_2$ 2H$_2$O, 1.0 g of Bacto Peptone, 5.0 g of yeast extract, 0.2 g of MgSO$_4$ 7H$_2$O, 4.0 g of K$_2$HPO$_4$, 1.0 ml of COVE trace elements solution, 2.5 g of glucose, 25.0 g of pretreated corn stover (PCS), and deionized water to 1 liter.

COVE trace elements solution was composed of 0.04 g of Na$_2$B$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_2$.2H$_2$O, 10 g of ZnSO$_4$.7H$_2$O, and deionized water to 1 liter.

YPM medium was composed of 1% yeast extract, 2% Bacto peptone, and 2% maltose. Minimal medium plates were composed of 6 g of NaNO$_3$, 0.52 of KCl, 1.52 g of KH$_2$PO$_4$, 1 ml of COVE trace metals solution, 20 g of Noble agar, 20 ml of 50% glucose, 2.5 ml of 20% MgSO$_4$.7H$_2$O, 20 ml of biotin stock solution, and deionized water to 1 liter.

Biotin stock solution was composed of 0.2 g of biotin and deionized water to 1 liter.

COVE trace metals solution was composed per liter of 0.04 g of Na$_2$B$_4$O$_7$.10H$_2$O, 0.4 g of CuSO$_4$.5H$_2$O, 1.2 g of FeSO$_4$.7H$_2$O, 0.7 g of MnSO$_4$.H$_2$O, 0.8 g of Na$_2$MoO$_2$.H$_2$O, 10 g of ZnSO$_4$.7H$_2$O, and deionized water to 1 liter.

Example 1

Preparation of *Penicillium* Sp. Strain Mycelia for Total RNA Extraction

A compost sample was collected from Yunnan, China. *Penicillium* sp. NN051602 was isolated using single spore isolation techniques on PDA plates at 45° C. The *Penicillium* sp. strain was inoculated onto a PDA plate and incubated for 4 days at 45° C. in the darkness. Several mycelia-PDA plugs were inoculated into 500 ml shake flasks containing 100 ml of NNCYP-PCS medium. The flasks were incubated for 6 days at 45° C. with shaking at 160 rpm. The mycelia were collected at day 4, day 5, and day 6. Then the mycelia from each day were combined and frozen in liquid nitrogen, and then stored in a −80° C. freezer until use.

Example 2

*Penicillium* Sp. Strain RNA Preparation

The frozen mycelia were transferred into a liquid nitrogen prechilled mortar and pestle and ground to a fine powder. Total RNA was prepared from the powdered mycelia by extraction with TRIZOL® reagent (Invitrogen, Carlsbad, Calif., USA) and purified using a RNEASY® Mini Kit (QIAGEN Inc., Valencia, Calif., USA) according to the manufacturer's protocol. Fifty micrograms of total RNA was submitted to sequencing as described in Example 3.

Example 3

Sequence Assembly and Mining

Total RNA enriched for polyA sequences with the mRNASeq protocol was sequenced using an ILLUMINA® GA2 system (Illumina, Inc., San Diego, Calif., USA). The raw 36 base pair reads were assembled with an in-house assembler. The assembled sequences were analyzed using standard bioinformatics methods for gene finding and functional prediction. ESTScan 2.0 was used for gene prediction. NCBI blastall version 2.2.10 and HMMER version 2.1.1 were used to predict function based on structural homology. The Family GH61 candidate was identified directly by analysis of the Blast results.

Example 4

Preparation of Penicillium Sp. NN051602 Genomic DNA

*Penicillium* sp. NN051602 was grown on a PDA plate at 45° C. for 3 days. Mycelia were collected directly from the agar plate into a sterilized mortar and frozen under liquid nitrogen. Frozen mycelia were ground, by mortar and pestle, to a fine powder, and genomic DNA was isolated using a DNEASY® Plant Mini Kit (QIAGEN Inc., Valencia, Calif., USA).

Example 5

Cloning of the *Penicillium* Sp. GH61 Gene from Genomic DNA

Based on the ILLUMINA® sequencing information of the *Penicillium* sp. GH61 gene obtained in Example 3, oligonucleotide primers, shown below, were designed to amplify the GH61 polypeptide gene from genomic DNA of *Penicillium* sp. NN051602. An IN-FUSION® CF Dry-down Cloning Kit (Clontech Laboratories, Inc., Mountain View, Calif., USA) was used to clone the fragment directly into the expression vector pPFJO355, without the need for restriction digestion and ligation.

```
Sense primer:
                                            (SEQ ID NO: 3)
5'-ACACAACTGGGGATCCACCATGCTGTCTTCGACGACTCGCA-3'

Antisense primer:
                                            (SEQ ID NO: 4)
5'-GTCACCCTCTAGATCTCGACTTCTTCTAGAACGTCGGCTCA-3'
```

Bold letters represented the coding sequence and the remaining sequence was homologous to insertion sites of pPFJO355.

The expression vector pPFJO355 contains the *Aspergillus oryzae* TAKA-amylase promoter, *Aspergillus niger* glucoamylase terminator elements, pUC19 derived sequences for selection and propagation in *E. coli*, and a pyrG gene, which encodes an *Aspergillus nidulans* orotidine decarboxylase for selection of a transformant of a pyrG mutant *Aspergillus* strain.

Twenty picomoles of each of the primers above were used in a PCR reaction composed of *Penicillium* sp. NN051602 genomic DNA, 10 µl of 5×GC Buffer (Finnzymes Oy, Espoo, Finland), 1.5 µl of DMSO, 2.5 mM each of dATP, dTTP, dGTP, and dCTP, and 0.6 unit of PHUSION™ High-Fidelity DNA Polymerase (Finnzymes Oy, Espoo, Finland) in a final volume of 50 µl. The amplification was performed using a Peltier Thermal Cycler (M J Research Inc., South San Francisco, Calif., USA) programmed for denaturing at 98° C. for 1 minutes; 5 cycles of denaturing at 98° C. for 15 seconds, annealing at 63° C. for 30 seconds, with a 1° C. increase per cycle and elongation at 72° C. for 60 seconds; 25 cycles each at 98° C. for 15 seconds and 72° C. for 60 seconds; and a final extension at 72° C. for 5 minutes. The heat block then went to a 4° C. soak cycle.

The reaction products were isolated by 1.0% agarose gel electrophoresis using 90 mM Tris-borate and 1 mM EDTA (TBE) buffer where an approximately 0.9 kb product band was excised from the gel, and purified using an ILLUSTRA® GFX® PCR DNA and Gel Band Purification Kit (GE Healthcare, Buckinghamshire, UK) according to the manufacturer's instructions.

Plasmid pPFJO355 was digested with Bam I and Bgl II, isolated by 1.0% agarose gel electrophoresis using TBE buffer, and purified using an ILLUSTRA® GFX® PCR DNA and Gel Band Purification Kit according to the manufacturer's instructions.

The gene fragment and the digested vector were ligated together using an IN-FUSION® CF Dry-down PCR Cloning Kit resulting in pGH61D23Y4 (FIG. 1) in which transcription of the *Penicillium* sp. GH61 gene was under the control of the *Aspergillus oryzae* TAKA-alpha-amylase promoter. In brief, 30 ng of pPFJO355 digested with Bam I and Bgl II, and 60 ng of the *Penicillium* sp. GH61 gene purified PCR product were added to a reaction vial and resuspended in a final volume of 10 µl with addition of deionized water. The reaction was incubated at 37° C. for 15 minutes and then 50° C. for 15 minutes. Three µl of the reaction were used to transform *E. coli* TOP10 competent cells (TIANGEN Biotech Co. Ltd., Beijing, China). An *E. coli* transformant containing pGH61 D23Y4 was detected by colony PCR and plasmid DNA was prepared using a QIAprep Spin Miniprep Kit (QIAGEN Inc., Valencia, Calif., USA). The *Penicillium* sp. GH61 gene insert in pGH61 D23Y4 was confirmed by DNA sequencing using a 3730XL DNA Analyzer (Applied Biosystems Inc, Foster City, Calif., USA).

The same PCR fragment was cloned into vector pGEM-T (Promega Corporation, Madison, Wis., USA) using a pGEM-T Vector System (Promega Corporation, Madison, Wis., USA) to generate pGEM-T-GH61D23Y4. The *Penicillium* sp. GH61 gene insert in pGEM-T-GH61 D23Y4 was confirmed by DNA sequencing using a 3730XL DNA Analyzer. *E. coli* strain T-51602 designated *E. coli* NN059154, containing pGEM-T-GH61D23Y4, was deposited with the Deutsche Sammlung von Mikroorganismen und Zellkulturen GmbH (DSM), Mascheroder Weg 1 B, D-38124 Braunschweig, Germany on Aug. 26, 2009 and assigned accession number DSM 22882.

Example 6

Characterization of the *Penicillium* Sp. Genomic Sequence Encoding a GH61A Polypeptide Having Cellulolytic-Enhancing Activity DNA sequencing of the *Penicillium* sp. genomic clone encoding a GH61A polypeptide having cellulolytic-enhancing activity was performed with an Applied Biosystems Model 3700 Automated DNA Sequencer using version 3.1 BIG-DYE™ terminator chemistry (Applied Biosystems, Inc., Foster City, Calif., USA) and dGTP chemistry (Applied Biosystems, Inc., Foster City, Calif., USA) and primer walking strategy. Nucleotide sequence data were scrutinized for quality and all sequences were compared to each other with assistance of PHRED/PHRAP software (University of Washington, Seattle, Wash., USA).

The nucleotide sequence (SEQ ID NO: 1) and deduced amino acid sequence (SEQ ID NO: 2) of the *Penicillium* sp. gh61a gene are shown in FIG. 2. The coding sequence is 835 bp including the stop codon and is interrupted by one intron of 73 bp (nucleotides 114-186). The encoded predicted protein is 253 amino acids. The % G+C of the coding sequence of the gene (including introns) is 63.35% G+C and the mature polypeptide coding sequence is 64.62%. Using the SignalP program (Nielsen et al., 1997, *Protein Engineering* 10:1-6), a signal peptide of 25 residues was predicted. The predicted mature protein contains 228 amino acids with a predicted molecular mass of 24.33 kDa and an isoelectric point of 4.17.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Penicillium* gene encoding the GH61A polypeptide having cellulolytic-enhancing activity shares 74% identity (excluding gaps) to the deduced amino acid sequence of a predicted GH61 family protein from *Thermoascus aurantiacus* (GENESEQP:AUM17198).

Example 7

Expression of *Penicillium* Sp. GH61A Gene in *Aspergillus oryzae*

*Aspergillus oryzae* HowB101 (WO 95/35385 Example 1) protoplasts were prepared according to the method of Christensen et al., 1988, Bio/Technology 6: 1419-1422 and transformed with 3 µg of pGH61D23Y4. The transformation yielded about 50 transformants. Twelve transformants were isolated to individual Minimal medium plates.

Six transformants were inoculated separately into 3 ml of YPM medium in a 24-well plate and incubated at 30° C., 150 rpm. After 3 days incubation, 20 μl of supernatant from each culture were analyzed on a NuPAGE® Novex 4-12% Bis-Tris Gel with 2-(N-morpholino)ethanesulfonic acid (MES) (Invitrogen Corporation, Carlsbad, Calif., USA) according to the manufacturer's instructions. The resulting gel was stained with INSTANT® Blue (Expedeon Ltd., Babraham Cambridge, UK). SDS-PAGE profiles of the cultures showed that the majority of the transformants had a major band of approximately 45 kDa. The expression strain was designated *Aspergillus oryzae* EXP03089.

A slant of *Aspergillus oryzae* EXP03089 was washed with 10 ml of YPM medium and inoculated into a 2 liter flask containing 400 ml of YPM medium to generate broth for characterization of the enzyme. The culture was harvested on day 3 and filtered using a 0.45 μm DURAPORE Membrane (Millipore, Bedford, Mass., USA).

Example 8

Purification of Recombinant *Penicillium* Sp. GH61 Polypeptide Having Cellulolytic Enhancing Activity from *Aspergillus oryzae*

A 400 ml volume of the filtered broth of the recombinant strain *Aspergillus oryzae* EXP03089 was precipitated with ammonium sulfate (80% saturation) and redissolved in 20 ml of 25 mM sodium acetate pH 5.0 buffer, and then dialyzed against the same buffer and filtered through a 0.45 mm filter. The solution was applied to a 30 ml Q SEPHAROSE® Fast Flow column (GE Healthcare, Buckinghamshire, UK) equilibrated in 25 mM sodium acetate pH 5.0. The recombinant GH61 protein was eluted with a linear NaCl gradient (0-0.4 M). Fractions eluted with 0.1-0.2 M NaCl were collected and dialyzed against the same equilibration buffer. The sample was further purified on a MONO Q® column (GE Healthcare, Buckinghamshire, UK) with a linear NaCl gradient (0-0.3 M). Fractions were evaluated by SDS-PAGE. Fractions containing a band of approximately 45 kDa were pooled. The pooled solution was concentrated by ultrafiltration.

Example 9

Hydrolysis of Pretreated Corn Stover by *Penicillium* Sp. Polypeptide Having Cellulolytic Enhancing Activity Culture broth was prepared as described in Example 7 and concentrated approximately 20-fold using an Amicon ultrafiltration device (Millipore, Bedford, Mass., USA, 10 kDa polyethersulfone membrane, 40 psi, 4° C.). Protein concentration was estimated by densitometry following SDS-PAGE and Coomassie blue staining. Corn stover was pretreated and prepared as an assay substrate as described in WO 2005/074647 to generate pretreated corn stover (PCS). The base cellulase mixture used to assay enhancing activity was prepared from *Trichoderma reesei* strain SMA135 (WO 2008/057637).

Hydrolysis of PCS was conducted using 1.6 ml deep-well plates (Axygen, Santa Clara, Calif., USA) using a total reaction volume of 1.0 ml and a PCS concentration of 50 mg/ml in 1 mM manganese sulfate-50 mM sodium acetate, pH 5.0. The *Penicillium* sp. GH61 polypeptide was separately added to the base cellulase mixture at concentrations ranging from 0 to 100% of the protein concentration of the base cellulase mixture. Incubation was at 50° C. for 72 hours. Assays were performed in triplicate. Aliquots were centrifuged, and the supernatant liquid was filtered by centrifugation (MULTISCREEN® HV 0.45 μm, Millipore, Billerica, Mass., USA) at 3000 rpm for 10 minutes using a plate centrifuge (SORVALL® RT7, Thermo Fisher Scientific, Waltham, Mass., USA). When not used immediately, filtered hydrolysate aliquots were frozen at −20° C. Sugar concentrations of samples diluted in 0.005 M $H_2SO_4$ with 0.05% w/w benzoic acid were measured after elution by 0.005 M $H_2SO_4$ with 0.05% w/w benzoic acid at a flow rate of 0.6 ml/minute from a 4.6×250 mm AMINEX® HPX-87H column (Bio-Rad Laboratories, Inc., Hercules, Calif., USA) at 65° C. with quantitation by integration of glucose and cellobiose signals from refractive index detection (CHEMSTATION®, AGILENT® 1100 HPLC, Agilent Technologies, Santa Clara, Calif., USA) calibrated by pure sugar samples (Absolute Standards Inc., Hamden, Conn., USA). The resultant equivalents were used to calculate the percentage of cellulose conversion for each reaction. The degree of cellulose conversion to glucose plus cellobiose sugars (conversion, %) was calculated using the following equation:

$$\text{Conversion}(\%) = (\text{glucose} + \text{cellobiose} \times 1.053)(\text{mg/ml}) \times 100 \times 162/(\text{Cellulose (mg/ml)} \times 180) = (\text{glucose} + \text{cellobiose} \times 1.053)(\text{mg/ml}) \times 100/(\text{Cellulose (mg/ml)} \times 1.111)$$

In this equation the factor 1.111 reflects the weight gain in converting cellulose to glucose, and the factor 1.053 reflects the weight gain in converting cellobiose to glucose. Cellulose in PCS was determined by a limit digest of PCS to release glucose and cellobiose.

Figure 3:
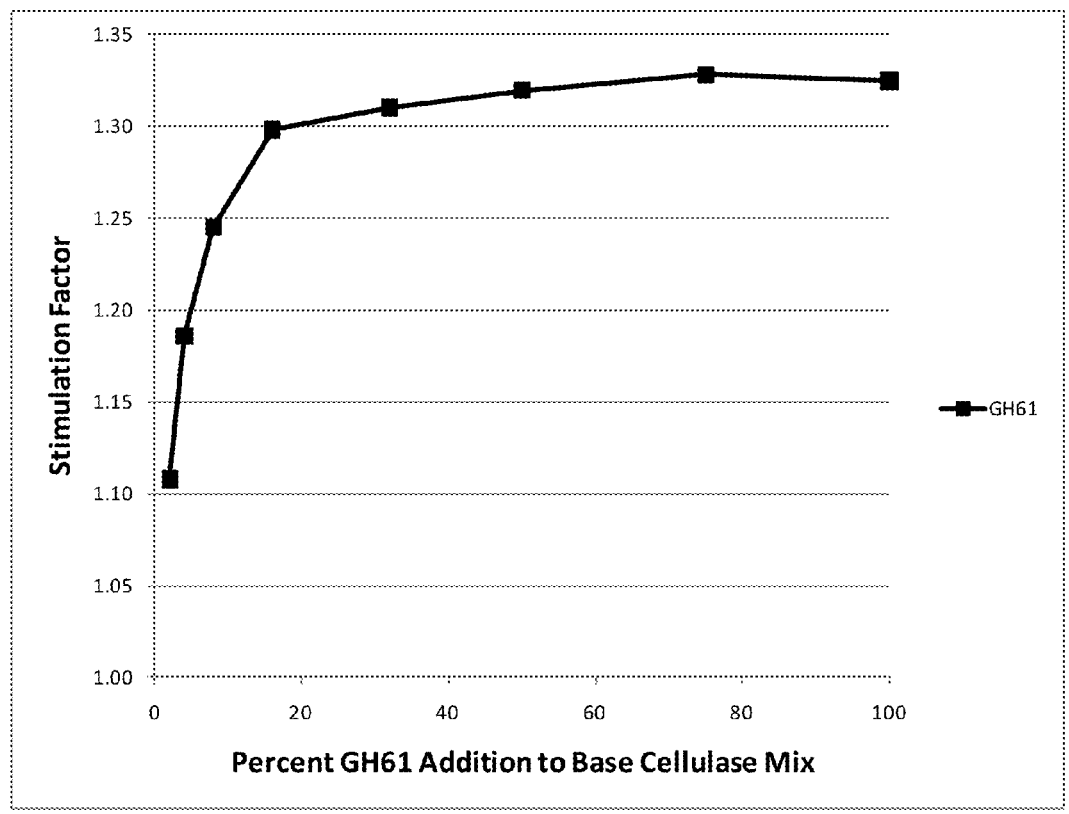
FIG. 3 shows hydrolysis vs. concentration of added *Penicillium* sp. GH61A polypeptide having cellulolytic enhancing activity.

The results of adding increasing amounts of the *Penicillium* sp. GH61 polypeptide to the base cellulase mix are shown in FIG. 3. Addition of the *Penicillium* sp. GH61 polypeptide provided a stimulation factor of 1.29 at a 100% addition level.

Deposit of Biological Material

The following biological material has been deposited under the terms of the Budapest Treaty with the Deutsche Sammlung von Mikroorganismen and Zellkulturen GmbH (DSM), Mascheroder Weg 1 B, D-38124 Braunschweig, Germany, and given the following accession number:

| Deposit | Accession Number | Date of Deposit |
| --- | --- | --- |
| *E. coli* (NN059154) | DSM 22882 | Aug. 26, 2009 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An isolated polypeptide having cellulolytic enhancing activity, comprising an amino acid sequence having at least 90% sequence identity to amino acids 26 to 253 of SEQ ID NO: 2.

2. A method for degrading a cellulosic material, comprising: treating the cellulosic material with an enzyme composition comprising one or more cellulolytic enzymes in the presence of the polypeptide having cellulolytic enhancing activity of claim 1.

3. The method of claim 2, further comprising recovering the degraded cellulosic material.

4. The method of claim 3, wherein the degraded cellulosic material is a sugar.

5. The method of claim 2, wherein the cellulosic material is pretreated.

6. The method of claim 2, wherein the enzyme composition comprises one or more enzymes selected from the group consisting of a cellulase, a hemicellulase, an esterase, an expansin, a ligninolytic enzyme, a pectinase, a peroxidase, a protease, and a swollenin.

7. A method for producing a fermentation product, comprising:
(a) saccharifying a cellulosic material with an enzyme composition in the presence of the polypeptide having cellulolytic enhancing activity of claim 1;
(b) fermenting the saccharified cellulosic material with one or more fermenting microorganisms to produce the fermentation product; and
(c) recovering the fermentation product from the fermentation.

8. The method of claim 7, wherein the cellulosic material is pretreated.

9. The method of claim 7, wherein steps (a) and (b) are performed simultaneously in a simultaneous saccharification and fermentation.

10. The method of claim 7, wherein the enzyme composition comprises one or more enzymes selected from the group consisting of a cellulase, a hemicellulase, an esterase, an expansin, a ligninolytic enzyme, a pectinase, a peroxidase, a protease, and a swollenin.

11. A method of fermenting a cellulosic material, comprising: fermenting the cellulosic material with one or more fermenting microorganisms, wherein the cellulosic material is saccharified with an enzyme composition in the presence of a polypeptide having cellulolytic enhancing activity of claim 1.

12. The method of claim 11, wherein the fermenting of the cellulosic material produces a fermentation product.

13. The method of claim 11, wherein the cellulosic material is pretreated before saccharification.

14. The method of claim 11, wherein the enzyme composition comprises one or more enzymes selected from the group consisting of a cellulase, a hemicellulase, an esterase, an expansin, a ligninolytic enzyme, a pectinase, a peroxidase, a protease, and a swollenin.

* * * * *

SEQUENCE LISTING

<160> NUMBER OF SEQ ID NOS: 4

<210> SEQ ID NO 1
<211> LENGTH: 835
<212> TYPE: DNA
<213> ORGANISM: Penicillium sp.

<400> SEQUENCE: 1

```
atgctgtctt cgacgactcg caccctcgcc tttacaggcc ttgcgggcct tctgtccgct    60
cccctggtca aggcccatgg ctttgtccag ggcattgtca tcggtgacca attgtaagtc   120
cctctcttgc agttctgtcg attaactgct ggactgcttg cttgactccc tgctgactcc   180
caacagctac agcgggtaca tcgtcaactc gttccctac gaatccaacc caccccccgt    240
catcggctgg gccacgaccg ccaccgacct gggcttcgtc gacggcacag gataccaagg   300
cccggacatc atctgccacc ggaatgcgac gcccgcgccg ctgacagccc ccgtggccgc   360
cggcggcacc gtcgagctgc agtggacgcc gtggccggac agccaccacg gacccgtcat   420
cacctacctg gcgccgtgca acggcaactg ctcgaccgtc gacaagacga cgctggagtt   480
cttcaagatc gaccagcagg gcctgatcga cgacacgagc ccgccgggca cctgggcgtc   540
ggacaacctc atcgccaaca caatagctg gaccgtcacc attcccaaca gcgtcgcccc    600
cggcaactac gtcctgcgcc acgagatcat cgccctgcac tcggccaaca acaaggacgg   660
cgcccagaac taccccagt gcatcaacat cgaggtcacg gcggcggct ccgacgcgcc     720
tgagggtact ctgggcgagg atctctacca tgacaccgac ccgggcattc tggtcgacat   780
ttacgagccc attgcgacgt ataccattcc ggggccgcct gagccgacgt tctag        835
```

<210> SEQ ID NO 2
<211> LENGTH: 253
<212> TYPE: PRT
<213> ORGANISM: Penicillium sp.

<400> SEQUENCE: 2

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175
```

```
Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250

<210> SEQ ID NO 3
<211> LENGTH: 41
<212> TYPE: DNA
<213> ORGANISM: Penicillium sp.

<400> SEQUENCE: 3
acacaactgg ggatccacca tgctgtcttc gacgactcgc a                    41

<210> SEQ ID NO 4
<211> LENGTH: 41
<212> TYPE: DNA
<213> ORGANISM: Penicillium sp.

<400> SEQUENCE: 4
gtcaccctct agatctcgac ttcttctaga acgtcggctc a                    41
```